United States Patent [19]

Shriver et al.

[11] Patent Number: 5,166,050

[45] Date of Patent: Nov. 24, 1992

[54] MONOCLONAL ANTIBODIES AND PEPTIDES USEFUL IN TREATING AND DIAGNOSING HIV INFECTIONS

[75] Inventors: Mary K. Shriver, Bellevue; Larry H. Gosting, Snohomish; Edna S. Dickinson, Seattle; Janela McClure, City of Vashon Is.; Elaine K. Thomas, Seattle; Wesley L. Cosand, Bothell, all of Wash.

[73] Assignee: Bristol-Myers Squibb Company, New York, N.Y.

[21] Appl. No.: 625,777

[22] Filed: Dec. 7, 1990

Related U.S. Application Data

[63] Continuation of Ser. No. 547,428, Jul. 3, 1990, abandoned, which is a continuation of Ser. No. 45,026, May 1, 1987, abandoned, which is a continuation-in-part of Ser. No. 898,273, Aug. 20, 1986, abandoned.

[51] Int. Cl.$^5$ .................. G01N 33/569; C12N 5/20; C07K 15/28; A61K 39/42
[52] U.S. Cl. .................. 435/5; 435/70.21; 435/172.2; 435/240.27; 530/388.1; 530/388.35; 530/389.4; 530/864; 530/868; 424/85.8; 424/86
[58] Field of Search ............ 435/70.21, 172.2, 240.27, 435/5; 530/388.1, 388.35, 389.4; 424/85.8, 86, 89

[56] References Cited

U.S. PATENT DOCUMENTS

| | | | |
|---|---|---|---|
| 4,743,678 | 5/1988 | Essex et al. | 435/5 |
| 4,753,873 | 6/1988 | Beltz et al. | 435/5 |
| 4,755,457 | 7/1988 | Robert-Guroff et al. | 435/5 |
| 4,956,273 | 9/1990 | Kennedy et al. | 435/5 |

FOREIGN PATENT DOCUMENTS

| | | | |
|---|---|---|---|
| 181150 | 5/1986 | European Pat. Off. | |
| 185444 | 6/1986 | European Pat. Off. | |
| 199301 | 10/1986 | European Pat. Off. | |
| 201176 | 11/1986 | European Pat. Off. | |
| 219106 | 4/1987 | European Pat. Off. | |
| 231914 | 8/1987 | European Pat. Off. | |
| 251612 | 1/1988 | European Pat. Off. | |
| 255190 | 2/1988 | European Pat. Off. | |
| 273716 | 7/1988 | European Pat. Off. | |
| 2188639A | 10/1987 | United Kingdom . | |
| 86/02383 | 4/1986 | World Int. Prop. O. | |
| 86/04336 | 7/1986 | World Int. Prop. O. | |
| 86/04613 | 8/1986 | World Int. Prop. O. | 435/5 |
| 86/06099 | 10/1986 | World Int. Prop. O. | |
| 87/04728 | 8/1987 | World Int. Prop. O. | |
| 87/07616 | 12/1987 | World Int. Prop. O. | |
| 88/00471 | 1/1988 | World Int. Prop. O. | |

OTHER PUBLICATIONS

Fung et al, "Monoclonal Antibodies That Neutralize HIV-1 Virions and Inhibit Syncytium Formation by Infected Cells", Bio/Technology, 5 (1987) 940–942, 944–946.

Chanh et al, "Human immunodeficiency virus gp120 glycoprotein detected by a monoclonal antibody to a synthetic peptide", Eur. J. Immunol., 16 (1986) 1465–1468.

Caruso et al, "Liquid competition radioimmunoassay for the detection and quantitation of the HIV p24", J. Virol. Meth., 17 (1987) 199–210.

Ferns et al, "Characterization of Monoclonal Antibodies Against the Human Immunodeficiency Virus (HIV) gag Products and Their Use in Monitoring HIV Isolate Variation", J. Gen. Vir., 68 (1987) 1543–1551.

Beretta et al, "HIV env glycoprotein shares a cross-reacting epitope with a surface protein present on activated human monocytes and involved in antigen presentation", Eur. J. Immunol., 17 (1987) 1793–8.

di Marzo Veronese et al, "Biochemical and Immunological Analysis of Human Immunodeficiency Virus gag Gene Products p17 and p24", J. Virol., 62 (1987) 795–801.

Banapour et al, "Characterization and Epitope Mapping of a Human Monoclonal Antibody Reactive with the Envelope Glycoprotein of Human Immunodeficiency Virus", J. Immunol., 139 (1987) 4027–4033.

Ghrayeb et al, "Human T–Cell Lymphotropic Virus Type III (HTLV-III) Core Antigens: Synthesis in *Escherichia coli* and Immunoreactivity with Human Sera", DNA, 5 (1986) 93–99.

Lasky et al, "Delineation of a Region of the Human Immunodeficiency Virus Type 1 gp120 Glycoprotein Critical for Interaction with the CD4 Receptor", Cell, 50 (1987) 975–985.

Hattori et al, "Characterization of Three Monoclonal Antibodies (VAK3-5) That Identify p24, Core Protein of Human Immunodeficiency Virus, and Its Precursors", Jpn. J. Cancer Res. (Gann), 78 (1987) 235–241.

Kennedy et al, "Synthetic Peptides Identify Native Antigenic Determinants Associated with Human T–Lymphotropic Virus Type III", Protides Biol. Fluids, 34 (1986) 107–110.

Hausmann et al, "Detection of HIV envelope specific antibodies by immunoelectron microscopy and correlation with anitbody titer and neutralizing activity", J. Virol. Meth., 16 (1987) 125–137.

(List continued on next page.)

*Primary Examiner*—John J. Doll
*Assistant Examiner*—Robert D. Budens
*Attorney, Agent, or Firm*—Townsend and Townsend

[57] ABSTRACT

Methods and composition for HIV diagnosis and treatment using monoclonal antibodies reactive with one or more neutralizing regions of HIV proteins, using the peptides or homologs thereof from that region, and using related nucleic acid segments. Exemplary neutralizing regions include selected portions of the env and gag genes from various HIV isolates. Monoclonal antibody secreting cell lines include HIV-gp110-1, -2, -3, -4, -5 and -6 (A.T.C.C. Accession Nos. HB9175, HB9176, HB9177, HV9405, HB9406 and HB9404, respectively) and HIV-p25-2, -3, -6 and -7 (A.T.C.C. Accession Nos. HB9407, HB9408, HB9409 and HB9410, respectively).

17 Claims, No Drawings

OTHER PUBLICATIONS

Palker et al, "A conserved region at the COOH terminus of human immunodeficiency virus gp120 envelope protein contains an immunodominant epitope", Proc. Nat'l. Acad. Sci. USA, 84 (1987) 2479-2483.

Matthews et al, "Restricted neutralization of divergent human T-lymphotropic virus type III isolates by antibodies to the major envelope glycoprotein", Proc. Nat'l. Acad. Sci. USA, 83 (1986) 9707-9713.

Chanh et al, "Induction of anti-HIV neutralizing antibodies by synthetic peptides", EMBO J., 5 (1986) 3065-3071.

Robey et al, "Prospect for prevention of human immunodeficiency virus infection: Purified 120-kDa envelope glycoprotein induces neutralizing antibody", Proc. Nat'l. Acad. Sci. USA, 83 (1986) 7023-7027.

Chassagne et al, "A Monoclonal Antibody Against LAV gag Precursor: Use for Viral Protein Analysis and Antigenic Expression in Infected Cells", J. Immunol., 136 (1986) 1442-1445.

Kennedy et al, "Use of a Resin-bound Synthetic Peptide for Identifying a Neutralizing Antigenic Determinant Associated with the Human Immunodeficiency Virus Envelope", J. Biol. Chem., 262 (1987) 5769-5774.

Groopman et al, "Characterization of Serum Neutralization Response to the Human Immunodeficiency Virus (HIV)", AIDS Res. Human Retroviruses, 3 (1987) 71-85.

Chanh et al, "Monoclonal anti-idiotypic antibody mimics the CD4 receptor and blinds human immunodeficiency virus", Proc. Nat'l. Acad. Sci. USA, 84 (1987) 3891-3895.

Robert-Guroff et al., *Nature* 316: 72-74 (1985).
McDougal et al., *Science* 231: 382-385 (1986).
Kennedy et al., *Science* 231: 1556-1559 (1986).
Starcich et al., *Cell* 45: 637-648 (1986).
Nakamura et al., *Intl. Conf. AIDS*, Abst. No. 506, (Jun., 1986).
Gosting et al., *Intl. Conf. AIDS*, Abst. No. 507, (Jun., 1986).
Lasky et al., *Science* 233: 209-213 (1986).
McDougal et al., *J. Immunol.* 137: 2937-2944 (1986).
Robert-Guroff et al., *J. Immunol.*, 137: 3306-3309 (1986).
Sattentau et al., *Science*, 234: 1120-1123 (1986).
Pert et al., *Proc. Natl. Acad. Sci. USA*, 83: 9254-9258 (1986).
Weiss et al., *Nature* 324: 572-575 (1986).
Putney et al., *Science* 234: 1392-1395 (1986).
Modrow et al., *J. Virol.* 61: 570-578 (1987).
Lasky et al., *J. Cell. Biochem.*, Suppl. 11D:33, Abst. 011, (1987).
Putney et al., *J. Cell. Biochem.*, Suppl. 11D:34, Abst. 013, (1987).
Dreesman et al., *J. Cell Biochem.*, Suppl. 11D:34, Abst. 014, (1987).
Palker et al., *J. Cell. Biochem.*, Suppl. 11D:46, Abst. 118, (1987).
Krohn et al., *J. Cell. Biochem.*, Suppl. 11D:54, Abst. 218, (1987).
Arthur et al., *J. Cell. Biochem.*, Suppl. 11D:63, Abst. 301, (1987).
Lyerly et al., *J. Cell. Biochem.*, Suppl. 11D:73, Abst. 403, (1987).
Ho et al., *J. Virol.* 61: 2024-2028 (1987).

MONOCLONAL ANTIBODIES AND PEPTIDES USEFUL IN TREATING AND DIAGNOSING HIV INFECTIONS

CROSS-REFERENCE TO RELATED APPLICATIONS

This is a continuation of application Ser. No. 07/547,428, filed Jul. 3, 1990, now abandoned, which is a continuation of Ser. No. 07/045,026, filed May 1, 1987, now abandoned, which is a continuation-in-part application of U.S. Ser. No. 898,273, filed Aug. 20, 1986, abandoned, which is incorporated herein by reference.

TECHNICAL FIELD

The present invention relates generally to the diagnosis, treatment and prevention of viral infections. More particularly, the invention provides compositions and methods for the production of monoclonal antibodies and peptides useful in diagnosing, neutralizing and vaccinating against Human Immunodeficiency Virus (HIV) infections.

BACKGROUND OF THE INVENTION

The infectious agent responsible for acquired immunodeficiency syndrome (AIDS) and its prodromal phases, AIDS-related complex (ARC) and lymphadenopathy syndrome (LAS), is a novel lymphotrophic retrovirus. The virus has been variously termed LAV, HTLV-III, ARV, and most recently HIV.

As the spread of HIV reaches pandemic proportions, the treatment of infected individuals and preventing the transmission to uninfected individuals at risk of exposure is of paramount concern. A variety of therapeutic strategies have targeted different stages in the life cycle of the virus and are outlined in Mitsuya and Broder, 1987, Nature 325:773. One approach involves the use of antibodies which bind to the virus and inhibit viral replication, either by interfering with viral entry into host cells or by some other mechanism. Once the viral component(s) susceptible to antibody intervention are identified, it is hoped that antibody titers sufficient to neutralize the infectivity of the virus could be engendered by vaccination or, alternatively, by the passive administration of immune globulins or monoclonal antibodies of the desired specificity.

The envelope glycoproteins of most retroviruses are thought to react with receptor molecules on the surface of susceptible cells, thereby determining (the virus' infectivity for certain hosts. Antibodies that bind to the glycoproteins may block the interaction of the virus with the cell receptors, neutralizing the infectivity of the virus. See generally, *The Molecular Biology of Tumor Viruses*, 534 (J. Tooze, ed., 1973) and *RNA Tumor Viruses*, 226, 236 (R. Weiss et al., eds., 1982), both of which are incorporated herein in their entirety by reference. See also, Gonzalez-Scarano et al., 1982, *Virology* 120:42 (La Crosse Virus); Matsuno and Inouye, 1983, *Infect. Immun.* 39:155 (Neonatal Calf Diarrhea Virus); and Mathews et al., 1982, *J. Immunol.*, 129:2763 (Encephalomyelitis Virus).

The general structure of HIV is that of a ribonucleoprotein core surrounded by a lipid-containing envelope which the virus acquires during the course of budding from the membrane of the infected host cell. Embedded within the envelope and projecting outward are the viral encoded glycoproteins. The envelope glycoproteins of HIV are initially synthesized in the infected cell as a precursor molecule of 150,000-160,000 daltons (gp150 or gp160), which is then processed in the cell into an N-terminal fragment of 110,000-120,000 daltons (gp110 or gp120) to generate the external glycoprotein, and a C-terminal fragment of 41,000-46,000 daltons (gp41), which represents the transmembrane envelope glycoprotein.

For the reasons discussed above, the gp110 glycoprotein of HIV has been the object of much investigation as a potential target for interrupting the virus' life cycle. Sera from HIV infected individuals have been shown to neutralize HIV in vitro, and antibodies that bind to purified gp110 are present in the sera Robert-Guroff et al., 1985, *Nature* 316:72; Weiss et al., 1985, *Nature* 316:69; and Mathews et al., 1986, *Proc. Natl. Acad. Sci. U.S.A.*, 83:9709. Purified and recombinant gp110 stimulated the production of neutralizing serum antibodies when used to immunize animals, Robey et al., 1986, *Proc. Natl. Acad. Sci. U.S.A.*, 83:7023; Lasky et al., 1986, *Science* 233:209; and a human, Zagury et al., 1986, *Nature* 326:249. Binding of the gp110 molecule to the CD4 (T4) receptor has also been shown, and monoclonal antibodies which recognize certain epitopes of the CD4 receptor have been shown to block HIV binding, syncytia formation and infectivity. McDougal et al., 1986, *Science* 231:382. Putney et al. (1986, *Science* 234:1392) elicited neutralizing serum antibodies in animals after immunizing with a recombinant fusion protein containing the carboxyl-terminal half of the gp110 molecule and further demonstrated that glycosylation of the envelope protein is unnecessary for a neutralizing antibody response.

A subunit vaccine for AIDS utilizing the HIV gp110 molecule or portions thereof may thus be desirable. Subunit vaccines are an alternative to vaccines prepared from inactivated or attenuated viruses. Inactivated vaccines are worrisome due to the possible failure to kill all of the viral particles, and attenuated viruses may possess the ability to mutate and regain their disease-causing capability. With subunit vaccines, only those portions of the virus that contain the antigens or epitopes that are capable of eliciting immune responses, i.e., neutralizing antibodies, ADCC, and cytotoxic T-cell response, are used to immunize the host. A major advantage of subunit vaccines is that irrelevant viral material is excluded.

Viral subunits for use in a vaccine can be generated by several methods. By way of example, the envelope glycoprotein can be expressed and purified from a bacterial host, although this molecule would lack most post-translational modifications (such as glycosylation) or other processing. Such modification may be obtained using a eukaryotic expression system, such as yeast or cultured mammalian cells. Viral genes have been introduced into mammalian cells using the vaccinia virus as a vector. See, for example, Mackett, M., et al., 1982, *Proc. Nat. Acad. Sci. U.S.A.* 79:7415; Panicali, D. and Paoletti, E., 1982, *Proc. Nat. Acad. Sci. U.S.A.* 79:4927. Recombinant vaccinia virus may be constructed according to the method of Hu et al., *Nature* 320:537 (1986) or Chakrabarti et al., *Nature* 320:535 (1986), both of which are incorporated herein by reference. In these systems viral glycoproteins produced by cells infected with recombinant vaccinia are appropriately glycosylated and may be transported to the cell surface for extrusion and ultimate isolation.

An important step in the production of a subunit vaccine is adequate purification of the desired glycoprotein from the complex mixture of the expression system. Several methods can be used to accomplish the purification. These include but are not limited to preparative polyacrylamide gel electrophoresis, gel permeation chromatography and various methods of chromatography (i.e., ion exchange, reverse phase, immunoaffinity, hydrophobic interaction) and others. Most of these methods are used in various combinations to achieve substantially pure preparations (Kleid, D. G., et al., 1981, *Science* 214:1125; Cabradilla, C. D., et al., 1986, *Biotechnology* 4:128, Dowbenko, D. J., 1985, *Proc. Nat. Acad. Sci. U.S.A.* 82:7748) which are incorporated herein by reference.

Methods which would reduce the number of steps required to achieve maximum purification of a particular viral antigen from a complex expression mixture are needed to manufacture subunit vaccines. The efficient separation of the antigens from extraneous components could be accomplished using immunoaffinity chromatography. This technique, also known as immunoadsorption, consists in principle of the selective adsorption of an antigen to a solid support on which a specific antibody has been covalently attached. The selectively adsorbed antigen is then eluted from such an antibody affinity adsorbent by changing, for example, the pH and/or ionic strength of the buffer.

Polyclonal antibodies, obtained from animals immunized with the desired antigen or from naturally infected individuals (see, for example, Lasky et al., supra), have frequently been used as immunoadsorbants, but, in general these reagents present substantial disadvantages, such as (i) not all of the antibodies bound to the insoluble support are specific for the molecule of interest, necessitating additional purification; (ii) yields of the desired antigen are frequently low; and (iii) antibody affinities often vary from one preparation to another, requiring modifications in elution procedures. The use of monoclonal antibodies specific for the desired viral antigen to be used in the subunit vaccine preparation, rather than polyclonal antibodies, would circumvent these difficulties.

Murine monoclonal antibodies that bind HIV antigens have been described. Several groups have reported monoclonal antibodies specific for the core protein p25 (see, for example, di Marzo Veronese, et al., 1985, *Proc. Nat. Acad. Sci. U.S.A.* 82:5199 and Chassagne, J., et al., 1986, *J. Immunol.* 136:1442). Monoclonal antibodies specific for the membrane glycoprotein gp41 have also been reported (see, for example, di Marzo Veronese, et al. 1985, *Science* 229:1402).

There remains a need in the art for monoclonal antibodies specific for epitopes within well defined regions of the major envelope glycoprotein, gp110. Monoclonal antibodies which bind these regions and cause a reduction in or elimination of the replication and transmissibility of HIV would have substantial therapeutic and prophylactic utility. Moreover, the monoclonal antibodies could also be used to purify the desired region of gp110 from disrupted virus or recombinant expression systems for use in vaccines, for example. Additionally, the region containing the epitope(s) recognized by the monoclonal antibodies could be chemically synthesized, thereby avoiding the difficulties inherent in purification and administration of larger fragments of the gp110 molecule. The present invention fulfills these and other related needs.

SUMMARY OF THE INVENTION

Peptides capable of immunologically mimicking neutralizing epitopes of HIV proteins, nucleic acid probes encoding such peptides and monoclonal antibodies reactive with such peptides are provided. These novel materials find use in, for example, diagnostics assays for the detection of HIV infections and in therapeutic regimens for the treatment of or vaccination against such infections.

DESCRIPTION OF THE SPECIFIC EMBODIMENTS

The present invention provides novel compositions and methods for neutralizing HIV infections, i.e., preventing or substantially inhibiting the formation or cellular transmission of infectious HIV in a host. More specifically, peptides mimicking a neutralizing region of HIV and monoclonal antibodies reactive with such a region are utilized to diagnose, treat and vaccinate against HIV infections. In this regard, the term "neutralizing region" indicates those portions of HIV, particularly HIV proteins, containing amino acid segments defining one or more epitopes reactive with antibodies which, either individually or in combination with other antibodies of the present invention, are capable of neutralizing HIV infections. Suitable assays for neutralization are well known and can include reduction of HIV infections in T-cell lines, reduction of plaque forming units of VSV(HIV) pseudotypes bearing the envelope glycoproteins of HIV, syncytial inhibition tests and virion-receptor binding tests. As desired, the neutralizing activity can be compared to antibody reactivity in immunochemical tests, such as immunofluorescence, immunoblot and radioimmunoprecipitation assay.

In one aspect, the novel peptides, typically less than about 50 amino acids, contain five or more contiguous amino acids forming epitopes substantially similar to epitopes located on neutralizing regions of HIV gp110 or p25, encoded by the env and gag regions, respectively, of the HIV genome. Of particular interest are the regions extending from about amino acid residue 301 to about 336 of gp110, and from about 278 to about 319 and from about 315 to about 363 of p25, all from the HIV strain designated LAV$_{BRU}$. The amino acid residue designations are from the Los Alamos Data Bank (AIDS virus sequence database, Los Alamos National Laboratory, Theoretical Division, Los Alamos, N.M. 87545).

Those skilled in the art will appreciate that additional analogous regions ("homologs") from other HIV isolates may be identified based upon their location within related proteins from various isolates. In practice, such homologs may be identified by reference to LAV$_{BRU}$ sequence data as follows:

(a) The amino acid sequences of HIV isolates and LAV$_{BRU}$ may be aligned to obtain maximum homology between the two sequences;

(b) Peptides comprising HIV isolates' amino acid sequences corresponding to the location of LAV$_{BRU}$ peptides that immunologically mimic LAV$_{BRU}$ proteins may be identified. The peptides comprising HIV isolate amino acid sequences so identified will typically immunologically mimic corresponding HIV isolate proteins.

This method can be applied to HIV strains that are yet to be discovered. For example, as new strains of HIV are identified, their envelope and core amino acid sequences may be aligned with that of LAV$_{BRU}$ to obtain maximum homology. The methods by which the sequences are aligned are known to those skilled in the art. In aligning the sequences it is desired to maintain as much homology between cysteine residues as possible. The amino acid sequence of the new HIV strain or species which corresponds to the location of the peptides specifically disclosed herein can be synthesized and used in accordance with the invention.

Another method for determining sequences of a homologous region in other HIV strains is described by Scharf et al., *Science* (1986) 233:1076. It employs two oligonucleotide primers which bind to conserved sequences outside the sequence region of interest, and contain different restrictive sites in each primer. DNA from HIV strains can then be amplified in vitro thereafter, the resulting oligonucleotides may be cloned in vectors for sequence analysis and incorporated into a vaccine as a cassette representing a particular epitope from the HIV strain.

It is not necessary to the present invention that the epitopes contained within such sequences be cross-reactive with antibodies to all strains or species of HIV. Peptides encompassing immunological epitopes which distinguish one species or serogroup over another will find utility in identifying particular species or serogroups, and may in fact assist in identifying individuals infected with one or more species or serogroups of HIV. They may also be useful in combination with other peptides, from either a homologous region or another neutralizing region, in therapeutic compositions.

The peptides of interest will most preferably be derived from the gp110 region of the virus. Of particular interest in this region are peptides encoded within the env open reading frame extending from about base pair (bp) 6667 to about 6774 of the $LAV_{BRU}$ isolate. Thus, various homologous regions of other HIV isolates include the homologous sequences obtained from Los Alamos Data Bank (except LAV2), as listed in Table I.

Other peptides suitable for generating or screening for monoclonal antibodies include those encoded in the env open reading frame from about bp 7246 to about 7317 of $LAV_{BRU}$. Such antibodies and reactive peptides are particularly useful in immunoassays.

In the gag region of the $LAV_{BRU}$ isolate, the p25 amino acid sequences from about 278 to 319 and 315 to 363 are additional neutralizing regions of HIV. Those skilled in the art will appreciate that additional neutralizing regions of HIV can be identified based on the teachings herein—in particular, combinations of monoclonal antibodies reactive with various different HIV epitopes will exhibit neutralizing activity.

Peptide I, also designated peptide 29, is encoded in the env open reading frame from about amino acid residue numbers 308 to about 328 and will have the following amino acid sequence, where oligopeptides included within the following sequence will include linear epitopes within such sequence:

I (29)

Y—Thr—Arg—Lys—Ser—Ile—Arg—Ile—Gln—Arg—Gly—Pro—Gly—Arg—Ala—Phe—Val—Thr—Ile—Gly—Lys—Ile—Y' in which Y and Y', when present, each represents sequences of up to about twenty amino acids.

TABLE I

| | | | |
|---|---|---|---|
| HXB2 | TGTACAAGACCCAACAACAATACAAGAAAAAGA . . . . . . . . . . . . . . . ATCCGTATC | | |
| | Cys Thr Arg Pro Asn Asn Asn Thr Arg Lys Arg . . . . . . . . . . . . . . . Ile Arg Ile | | 309 |
| BH102 | ———————————————————————————Ser ———————————————————————— | | 309 |
| BH8 | ———————————————————————————Lys ———————————————————————— | | 309 |
| HXB3 | ———————————————————————————Lys ———————————————————————— | | 309 |
| H9M | ———————————————————————————Ser ———————————————————————— | | 309 |
| BRU | ———————————————————————————Ser ———————————————————————— | | 314 |
| MAL | ————————————— Gly————————ArgGly ———————————————— His Phe | | 314 |
| ELI | —— Ala———————— Tyr Gln ——————————Gln— ———————————————Thr Pro——— | | 310 |
| ARV2 | ———————————————————————————Ser ————————————————————— Tyr——— | | 312 |
| WMJ2 | ————————————— Tyr———————— Val————————ArgSer ————————————————Leu Ser——— | | 306 |
| RFENV | ———————————————————————————Ser ———————————————————— Thr Lys | | 322 |
| Z6 | ————————————— Tyr Lys ——————————GlnSer ————————————————Thr Pro——— | | 311 |
| Z3 | ————————————— Gly Ser Asp Lys Lys Ile ———————————————————Gln Ser——— | | 306 |
| NY5 | ————————————————————— Lys———Gly ———————————————————— Ala——— | | 304 |
| CDC42 | ————————————————————— His——— Val Thr Leu . . . . . . . . . . . . . . | | 320 |
| LAV2 | ————————————— Gly———Lys——— Val———Gln ———————————————— Met Leu | | 302 |

| | | | |
|---|---|---|---|
| HXB2 | CAGAGA . . . . . . . . . . GGACCAGGGAGAGCATTTGTTACAATAGGAAAAATAGGAAATATG | | |
| | Gln Arg  Gly Pro Gly Arg Ala Phe Val Thr Ile Gly Lys Ile Gly Asn Met | | 326 |
| BH102 | ———————————————————————————————————————————————————— | | 326 |
| BH8 | ———————————————————————————————————————————————————— | | 326 |
| HXB3 | ———————————————————————————————————————————————————— | | 326 |
| H9M | ———————————————————————————————————————————————————— | | 326 |
| BRU | ———————————————————————————————————————————————————— | | 331 |
| MAL | . . . . . . ——————————————— Gln —— Leu Tyr —— Thr——— Ile Val———Asp Ile | | 329 |
| ELI | Gly Leu——————————— . . . Gln Ser Leu Tyr Thr —— Arg——— Ile Val Ser Arg Ser | | 323 |
| ARV2 | . . . . . . ——————————————————————— His —— Thr——— Arg———Ile Gly Asp | | 327 |
| WMJ2 | . . . . . . ——————————————————————— Arg —— Arg Glu . . . ——Ile Gly Ile | | 320 |
| RFENV | . . . . . . ——————————————————— Val Ile Tyr Ala Thr——— Gln———Ile Gly Asp | | 337 |
| Z6 | Gly Leu——————————— . . . Gln Ala Leu Tyr Thr —— Arg——— Arg Thr Lys Ile Ile | | 327 |
| Z3 | Arg Ile——————————————————— Lys Val —— Tyr Ala Lys——— Gly . . . . . . . . . . | | 319 |
| NY5 | Gly Pro——————————— . . . ——————— Thr Leu Tyr Ala Arg Glu . . . ——— Asp Ile | | 320 |
| CDC42 | . . . . . . . . . . . . . . . . . . . ——————— Val Trp Tyr —— Thr——— Glu———Leu Gly Asn | | 335 |
| LAV2 | Met Ser——————————————————— His Val —— His Ser His Tyr Gln Pro Ile——— Lys | | 323 |

TABLE I-continued

| | | | | | | | |
|---|---|---|---|---|---|---|---|
| HXB2 | . . . AGA . . . | | | CAAGCACATTGT | | | |
| | . . . Arg . . . | | | Gln Ala His Cys | | | 331 |
| BH102 | | | | | | | 331 |
| HXB3 | | | | | | | 331 |
| H9M | | | | | | | 331 |
| BRU | | | | | | | 336 |
| MAL | | | | Arg | Tyr | | 334 |
| ELI | Ile | Ile | Gly | | | | 330 |
| ARV2 | Ile | | Lys | . . . | | | 333 |
| WMJ2 | Ile | | | | | | 326 |
| RFENV | Ile | | Lys | . . . | | | 343 |
| Z6 | Gly . . . | | | | | | 334 |
| Z3 | Ile | Thr | Gly | | | | 326 |
| NY5 | | | | | | | 325 |
| CDC42 | Ile | | | | | | 341 |
| LAV2 | Arg | Pro | Arg | | Met | | 330 |

When Y and/or Y' are present, these may comprise, for example, one or more amino acids from sequences which flank amino acid residues 308 through 328 of the HIV envelope sequence or any portion of these flanking sequences. By way of example and not limitation, Y can comprise all or portions of the LAV$_{BRU}$ envelope amino acid sequence from about residue numbers 301 to 307; and Y' can comprise all or portions of the LAV-$_{BRU}$ envelope amino acid sequence from about residue numbers 329 to 336 as follows:

II (29a)

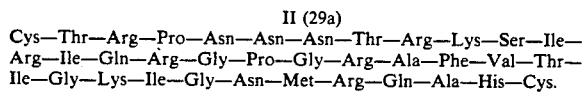

Cys—Thr—Arg—Pro—Asn—Asn—Asn—Thr—Arg—Lys—Ser—Ile—
Arg—Ile—Gln—Arg—Gly—Pro—Gly—Arg—Ala—Phe—Val—Thr—
Ile—Gly—Lys—Ile—Gly—Asn—Met—Arg—Gln—Ala—His—Cys.

Alternatively, truncated sequences of peptides of the present invention may be prepared. In this regard, the following sequences from peptide 29 may be particularly useful:

III (29b)

Y—Thr—Arg—Lys—Ser—Ile—Arg—Ile—Gln—Arg—Gly—Pro—Gly—
Y' in which Y and/or Y', when present, each represents sequences of up to about twenty or amino acid residues.

IV (29c)

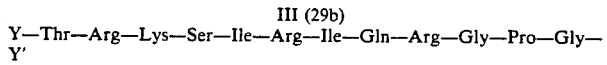

Y—Ile—Gln—Arg—Gly—Pro—Gly—Arg—Ala—Phe—Val—Thr—
Ile—Gly—Lys—Ile—Y' in which Y and Y', when present, each represents sequences of up to about twenty amino acid residues.

In another embodiment, homologous regions of the ARV-2 isolate of particular interest are encoded in the env open reading frame from about amino acid residue numbers 306 to about 323 and will typically have the following amino acid sequence, where oligopeptides included within the following amino acid sequence will include linear epitopes within such sequence:

V (177)

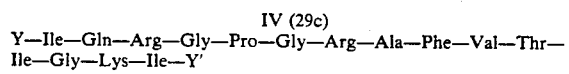

Y—Thr—Arg—Lys—Ser—Ile—Tyr—Ile—Gly—Pro—Gly—Arg—
Ala—Phe—His—Thr—Thr—Gly—Arg—Ile—Y' in which Y and Y', when present, each represents one up to about twenty or more amino acid residues. When Y and/or Y' are present, these may comprise one or more amino acid residues from sequences which flank amino acid residues 306 through 323 of the ARV-2 envelope sequence or any portion of these flanking sequences. In particular, Y can comprise all or portions of the HIV envelope amino acid sequence from about residue numbers 299 to 306; Y' can comprise all or portions of HIV envelope amino acid sequence from about residue numbers 324 to 333.

Alternatively, truncated sequences of peptide V may be prepared. In this regard, the following sequences may be particularly useful:

VI (177a)

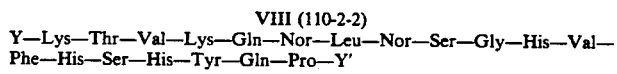

Y—Thr—Arg—Lys—Ser—Ile—Tyr—Ile—Gly—Pro—Gly—Y' in which Y and/or Y', when present, each represents sequences of up to twenty or more amino acid residues.

A further example comprises homologous regions of the LAV-2 isolate, such as encoded in the env open reading from about amino acid residue numbers 311 to 330, and will typically have the following sequence:

VIII (110-2-2)

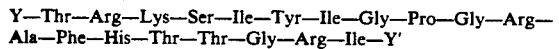

Y—Lys—Thr—Val—Lys—Gln—Nor—Leu—Nor—Ser—Gly—His—Val—
Phe—His—Ser—His—Tyr—Gln—Pro—Y' in which Y and/or Y', when present, each represents sequences of up to twenty or more amino acid residues. (See, *Nature* 326:662 (1987), which is incorporated herein by reference.)

In accordance with another aspect of the present invention, novel cell lines capable of producing monoclonal antibodies and compositions comprising such antibodies are provided, which antibodies are capable of selectively recognizing at extremely high titers (from $10^2$, to $10^4$ to about $10^7$ or more) neutralizing regions contained within a predetermined sequence of envelope glycoprotein gp110 or p25, their protein precursors, biologically-expressed recombinant fusion proteins and synthetic peptides that contain one or more epitopes within the predetermined sequence region of gp110 or p25. The subject hybrid cells have an identifiable chromosome, in which the germ line DNA has rearranged to encode an antibody having a binding site for an epitope on gp110 or p25 common to some or all HIV clinical isolates. These monoclonal antibodies may be used in a wide variety of ways including diagnosis and therapy, as well as to identify other cross-reactive antibodies, such as blocking antibodies. Peptides or polypeptides containing the epitope(s) with which they react may find separate uses as immunogens for vaccines, or as therapeutic agents.

Generation of Monoclonal Antibodies

The preparation of monoclonal antibodies can be accomplished by immortalizing the expression of nucleic acid sequences that code for antibodies specific for HIV, by introducing such sequences, typically cDNA encoding for the antibody, into a host capable of cultivation in culture. The immortalized cell line may be a mammalian cell line that has been transformed through oncogenesis, by transfection, mutation, or the like. Such cells include myeloma lines, lymphoma lines, or other cell lines capable of supporting the expression and secretion of the antibody in vitro. The antibody may be a naturally occurring immunoglobulin of a mammal, produced by transformation of a lymphocyte, particularly a splenocyte, by means of a virus or by fusion of the lymphocyte with a neoplastic cell, e.g., a myeloma, to produce a hybrid cell line. Typically, the splenocyte will be obtained from an animal immunized against the HIV virus or a fragment thereof containing an epitopic site.

Immunization protocols are well known and can vary considerably yet remain effective. See, Goding, *Monoclonal Antibodies: Principles and Practice,* Academic Press, 2nd edition (1986), which is incorporated herein by reference. Disrupted virus, synthetic peptides and bacterial fusion proteins which contain antigenic fragments of the gp110 or p25 molecule may be used as immunogens. Preferably the immunogen of disrupted virus, peptides or recombinant proteins will be enriched for proteins or fragments thereof containing the epitopes to which antibody-producing B cells or splenocytes are desired. More particularly, solutions containing disrupted virus lysates or extracts, or supernatants of biologically-expressed recombinant proteins or disrupted expression vectors, may be enriched for glycoproteins, as desired, using purification methods, such as, for example, polyacrylamide gel electrophoresis. Lectin affinity purification is a preferred and convenient method for purification of gp110 and other glycoproteins, e.g., affinity purification using lentil lectin. The extent to which the glycoproteins are purified from the solutions for use as an immunogen can vary widely, i.e., from less than 50%, usually or at least 75% to 95%, desirably 95% to 99% and, most desirably, to absolute homogeneity.

Once the proteins have been purified to the extent desired, they may be suspended or diluted in an appropriate physiological carrier for immunization, or may be coupled to an adjuvant. One preferred technique, for example, involves adsorbing the proteins and fragments thereof to lentil lectin agarose or other macromolecular carrier for injection. Immunogenic amounts of antigenic preparations enriched in HIV proteins, including gp110 glycoprotein and p25 core protein, or antigenic portions thereof, are injected, generally at concentrations in the range of 1 ug to 20 mg/kg of host. Administration may be by injection, e.g., intramuscularly, peritoneally, subcutaneously, intravenously, etc. Administration may be one or a plurality of times, usually at one to four week intervals. Immunized animals are monitored for production of antibody to the desired antigens, then the spleens are removed and splenic B-lymphocytes isolated and fused with a myeloma cell line or transformed. The transformation or fusion can be carried out in conventional ways, the fusion technique being described in an extensive number of patents, e.g., U.S. Pat. Nos. 4,172,124; 4,350,683; 4,363,799; 4,381,292; and 4,423,147. See also, Kennett et al., *Monoclonal Antibodies* (1980), and references therein, all of which are incorporated by reference, and Goding, supra.

The immortalized cell lines may be cloned and screened in accordance with conventional techniques, and antibodies in the cell supernatants detected that are capable of binding to the desired gp110 or p25 HIV viral proteins, recombinant fusion proteins or synthetic peptides which contain the desired epitopic region. The appropriate immortalized cell lines may then be grown in vitro or injected into the peritoneal cavity of an appropriate host for production of ascites fluid. By virtue of having some antibodies of the present invention, which are known to be specific for epitopes contained within the regions encoded by the LAV-$_{BRU}$ genomic region from about bp6688 to about bp6750 (encoding peptide 29), or from about bp7246 to about 7317 (encoding peptide 36) (bp numbering according to Wain-Hobson et al., Cell 44:9 1985, which is incorporated herein by reference), the supernatants may be screened in competition with the subject monoclonal antibodies in a competitive assay. Thus, immortalized hybridoma cell lines can be readily produced from a variety of sources based on the availability of the present antibodies specific for the particular antigen. Alternatively, these cell lines may be fused with other neoplastic B-cells, where such other B-cells may serve as recipients for genomic DNA coding for the antibody.

While rodent, particularly murine, neoplastic B-cells are preferred, other mammalian species may be employed, such as lagomorpha, bovine, ovine, equine, porcine, avian or the like. Immunization of these animals can be readily performed and their lymphocytes, particularly splenocytes, may be obtained for fusions.

The monoclonal antibody secreted by the transformed or hybrid cell lines may be of any of the classes or subclasses of immunoglobulins, such as IgM, IgD, IgA, $IgG_{1-4}$, or IgE. As IgG is the most common isotype utilized in diagnostic assays, it is often preferred. The monoclonal antibodies may be used intact, or as fragments, such as Fv, Fab, $F(ab')_2$, but usually intact.

To circumvent the possible antigenicity in a human host of a monoclonal antibody, derived from an animal other than human, chimeric antibodies may be constructed wherein the antigen binding fragment of an immunoglobulin molecule (variable region) is connected by a peptide linkage to at least part of another protein not recognized as foreign by humans, such as the constant portion of a human immunoglobulin molecule. This can be accomplished by fusing the animal variable region exons with human kappa or gamma constant region exons. Various techniques are known to the skilled artisan, such as those described in PCT 86/01533, EP171496, and EP173494, the disclosures of which are incorporated herein by reference.

Pharmaceutical Formulations and Use

The monoclonal antibodies of this invention that exhibit neutralizing activity, such as those which react with an epitopic site on gp110 or p25, can also be incorporated as components of pharmaceutical compositions. The composition should contain a therapeutic or prophylactic amount of at least one of the monoclonal antibodies of this invention with a pharmaceutically effective carrier. A pharmaceutical carrier should be any compatible, non-toxic substance suitable to deliver the monoclonal antibodies to the patient. Sterile water, alcohol, fats, waxes, and inert solids may be used as the carrier. Pharmaceutically acceptable adjuvants (buffering agents, dispersing agents) may also be incorporated into the pharmaceutical composition. Such compositions can contain a single monoclonal antibody so as to be, for example, specific for strains of HIV with envelope glycoproteins containing an epitopic site within a region encoded by bp6688-bp6750. Alternatively, a pharmaceutical composition can contain one or more monoclonal antibodies to form a "cocktail." For example, a cocktail containing monoclonal antibodies against the various strains of HIV would be a universal product with therapeutic or prophylactic activity against the great majority of the clinical isolates of HIV. The cocktail may contain monoclonal antibodies which bind to proteins or glycoproteins of HIV other than gp110 or p25, such as, for example, to gp41 glycoprotein, or p33 nuclease/integrase. The mole ratio of the various monoclonal antibody components will usually not differ by more than a factor of 10, more usually by not more than a factor of 5, and will usually be in a mole ratio of about 1:1-2 to each of the other antibody components.

The monoclonal antibodies of the present invention can be used as separately administered compositions given in conjunction with other anti-retroviral agents. The current status of the development of anti-retroviral agents, and of anti-HIV agents in particular, is reviewed in Mitsuya et al., Nature 325:773-778, 1987, which is incorporated herein by reference.

The monoclonal antibodies, peptides and pharmaceutical compositions thereof of this invention are particularly useful for oral or parenteral administration. Preferably, the pharmaceutical compositions may be administered parenterally, i.e., subcutaneously, intramuscularly or intravenously. Thus, this invention provides compositions for parenteral administration which comprise a solution of the monoclonal antibody, peptide or a cocktail thereof dissolved in an acceptable carrier, preferably an aqueous carrier. A variety of aqueous carriers can be used, e.g., water, buffered water, 0.4% saline, 0.3% glycine and the like. These solutions are sterile and generally free of particulate matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate, etc. The concentration of antibody in these formulations can vary widely, i.e., from less than about 0.5%, usually at or at least about 1% to as much as 15 or 20% by weight and will be selected primarily based on fluid volumes, viscosities, etc., preferably for the particular mode of administration selected.

Thus, a typical pharmaceutical composition for intramuscular injection could be made up to contain 1 ml sterile buffered water, and 50 mg of monoclonal antibody A typical composition for intravenous infusion could be made up to contain 250 ml of sterile Ringer's solution, and 150 mg of monoclonal antibody. Actual methods for preparing parenterally administrable compositions will be known or apparent to those skilled in the art and are described in more detail in, for example, *Remington's Pharmaceutical Science,* 15th Ed., Mack Publishing Company, Easton, Pa. (1980), which is incorporated herein by reference.

The monoclonal antibodies and peptides of this invention can be lyophilized for storage and reconstituted in a suitable carrier prior to use. This technique has been shown to be effective with conventional immune globulins and art-known lyophilization and reconstitution techniques can be employed. It will be appreciated by those skilled in the art that lyophilization and reconstitution can lead to varying degrees of antibody activity loss (e.g., with conventional immune globulins, IgM antibodies tend to have greater activity loss than IgG antibodies) and that use levels may have to be adjusted to compensate.

The compositions containing the present monoclonal antibodies, peptides or cocktails thereof can be administered for the prophylactic and/or therapeutic treatment of HIV infections. In therapeutic application, compositions are administered to a patient already infected with HIV, in an amount sufficient to cure or at least partially arrest the infection and its complications. An amount adequate to accomplish this is defined as a "therapeutically effective dose." Amounts effective for this use will depend upon the severity of the infection and the general state of the (patient's own immune system, but generally range from about 1 to about 200 mg of antibody per kilogram of body weight with dosages of from 5 to 25 mg per kilogram being more commonly used. It must be kept in mind that the materials of this invention may generally be employed in serious disease states, that is life-threatening or potentially life-threatening situations. In such cases, it is possible and may be felt desirable by the treating physician to administer substantial excesses of these antibodies.

In prophylactic applications, compositions containing the present antibodies or a cocktail thereof are administered to a patient not already infected by HIV, but perhaps recently exposed to or thought to have been exposed to, or at risk of being exposed to the virus, to enhance the patient's resistance to such potential infection or to vaccinate against the virus. An amount is defined to be a "prophylactically effective dose." In this use, the precise amounts again depend upon the patient's state of health and general level of immunity, but generally range from 0.1 mg to 25 mg per kilogram, especially 0.5 mg to 2.5 mg per kilogram.

Single or multiple administrations of the compositions can be carried out with dose levels and pattern being selected by the treating physician. In any event, the pharmaceutical formulations should provide a quantity of the antibody(ies) of this invention sufficient to effectively treat the patient.

In addition, the monoclonal antibodies of the present invention may find use as a target-specific carrier molecule. An antibody may be bound to a toxin to form an immunotoxin or a radioactive material or drug to form a radiopharmaceutical or pharmaceutical. Methods for producing immunotoxins and radiopharmaceuticals are well known (see, for example, *Cancer Treatment Reports* 68:317 (1984)).

It is also possible that heteroaggregates of monoclonal antibodies of the present invention and human T-cell activators, such as monoclonal antibodies to the CD3 antigen or to the $F_c$ gamma receptor on T-cells, may enable human T-cells or $F_c$-gamma bearing cells (such as K cells or neutrophils) to kill HIV infected cells via antibody dependent cell-mediated cytolysis (ADCC). Such heteroaggregates may be assembled, for example, by covalently cross-liking the anti-HIV antibodies to the anti-CD3 antibodies using the heterobifunctional reagent N-succinimidyl-3-(2-pyridyldithiol)-propionate, as described in Karpowsky et al., *J. Exp. Med.* 160:1686 (1984), which is incorporated by reference herein.

The subject peptide compositions themselves may also find use therapeutically, where administration results in the reduction or elimination of HIV in an infected host. These compositions, such as peptide 29 and peptide 126, the latter of which is disclosed in commonly owned pending application U.S. Ser. No. 930,785, incorporated by reference herein, may be administered in appropriate physiological carriers intravenously, subcutaneously, intramuscularly, intraperitoneally, etc. Various carriers include phosphate buffered saline, saline, water, potassium chloride, sodium lactate, or the like. The concentration of the peptide will vary widely depending on its ultimate use, activity, and mode of administration. Other anti-HIV agents may also be included in the formulations (other than the monoclonal antibodies which bind the peptides) such as 3'-azido-3'-deoxythymidine, 2',3'-dideoxycytidine, 2',3'-dideoxy-2',3'-didehydrocytidine, etc.

Use of Monoclonal Antibodies in Immunoaffinity Purification

Monoclonal antibodies specific for polypeptides containing gp110 or other antigenic determinants, particularly those antigenic determinants obtained from biologically-expressed recombinant fusion proteins or lysates or extracts of cultured HIV, are particularly advantageous for use in purification protocols. Generally the antibodies will have affinity association constants on the order of $10^8$ to $10^{12}$ M. Such antibodies may be used to purify the recombinant fusion proteins from the culture medium of the recombinant expression system if the expressed protein is secreted, or from the components of the disrupted biological expression system if it is not secreted. Generally, the monoclonal antibodies which are capable of reacting with gp110 or other antigenic determinants are attached to or immobilized on a substrate or support. The solution containing the HIV antigenic determinants is then contacted with the immobilized antibody under conditions suitable for the formation of immune complexes between the antibody and the polypeptides containing the gp110 antigenic determinants. Unbound material is separated from the bound immune complexes, which complexes or gp110 antigenic fragments are then separated from the support.

Typically, the monoclonal antibodies will be crudely purified from ascites fluid or cell culture supernatants prior to attachment to a support. Such procedures are well known by those skilled in the art, and may include fractionation with neutral salts at high concentration. Other methods, such as DEAE chromatography, gel filtration chromatography, preparative gel electrophoresis, or Protein A affinity chromatography, may also be used to purify the monoclonal antibody prior to its use as an immunoadsorbant.

The support to which the monoclonal antibodies are immobilized should have the following general characteristics: (a) weak interactions with proteins in general to minimize non-specific binding, (b) good flow characteristics which allow the flow through of high molecular weight materials, (c) possess chemical groups that can be activated or modified to allow chemical linkage of the monoclonal antibody, (d) physically and chemically stable in the conditions used to link the monoclonal antibody, and (e) stable to the conditions and constituents of the buffers required for adsorbtion and elution of the antigen. Some supports commonly used are agarose, derivatized polystyrenes, polysaccharides, polyacrylamide beads, activated cellulose, lose, glass and the like. Various chemical methods exist for the attachment of antibodies to substrate supports. See generally, Cuatrecasas, P., *Advances in Enzymology* 36:29 (1972). The antibodies of the present invention may be attached directly to the support or, alternatively, through a linker or spacer arm.

General conditions required for immobilization of monoclonal antibodies to chromatographic supports are well known in the art. See, for example, Tijssen, P., 1985, *Practice and Theory of Enzyme Immunoassay*, which is incorporated herein by reference. Actual coupling procedures will depend slightly on the characteristics and type of the antibody to be coupled. Monoclonal antibodies possess characteristics which are usually consistent from batch to batch, thereby allowing such conditions to be optimized. Attachment typically occurs through covalent bonds.

A suspension of extracts or lysates of HIV virus, the supernatant from a cultured biological expression system, or a suspension of the disrupted cells is then added to the separation matrix. The mixture is incubated under conditions and for a time sufficient for immune complex formation to occur, usually at least 30 minutes, more usually 2 to 24 hours. The immune complexes containing polypeptides with antigenic portions of gp110 are then separated from the mixture. Typically the mixture is removed, e.g., by elution, and the bound immune complexes extensively washed with adsorption buffer. The immune complexes may then be eluted from the separation matrix using eluant compatible with the particular support being used, which eluants are well known by those skilled in the art. Also, the polypeptides containing the gp110 or other antigenic portions may be selectively removed. For example, peptides that contain an epitope recognized by the antibodies can be used to compete for the antibody binding site, which presents an alternative elution technique that can be performed under mild elution conditions. The selectively adsorbed polypeptide containing the gp110 antigen may be eluted from an antibody affinity adsorbant by altering the pH and/or ionic strength of the buffer. Chaotropic agents may also find use in removing the bound antigen. The selection of a chaotropic agent, its concentration and other eluting conditions are dependent on the characteristics of the antibody-antigen interaction, but once determined should not be subject to changes usually necessary in polyclonal affinity separation systems.

The eluted material may require adjustment to a physiologic pH if low or high pH or ionic strength buffers are used to separate the bound gp110 antigens the separation matrix. Dialysis or gel filtration chromatography may also be required to remove excess from salts used in the eluent to permit reconstituton of gp110 or polypeptides containing antigenic fragments of gp110 to native conformations.

The methods of this invention yield, e.g., substantially purified gp110 or polypeptides containing antigenic fragments thereof, either naturally produced by infected cell cultures or by recombinant expression systems of bacteria, yeast, or cultured insect or mammalian cells. The gp110 and fragments or other purified proteins will typically be greater than 50% pure, more usually at least 75% pure, and frequently greater than 95% to 99% pure. These molecules may then find subsequent use in a wide variety of applications.

The HIV gp110 proteins, polypeptides containing the antigenic fragments thereof, or other proteins substantially purified according to the methods of the present invention, may find use in a wide variety of applications, including AIDS subunit vaccine formulations, in which the immunogen comprises an effective dose of antigenic determinants of, for example, gp110 or a neutralizing region thereof. Other components of the formulation would include those antigenic portions of HIV proteins or glycoproteins that stimulate the production of antibody (preferably neutralizing antibodies) in an immunized host, which antibodies are capable of protecting against subsequent infection by HIV.

Diagnostic Uses of Monoclonal Antibodies

Monoclonal antibodies of the present invention are also useful for diagnostic purposes. They can be either labeled or unlabeled for this purpose. Typically, diagnostic assays entail the detection of the formation of a complex through the binding of the monoclonal antibody to an HIV antigen. When unlabeled, the antibodies find use, for example, in agglutination assays. In addition, unlabeled antibodies can be used in combination with other labeled antibodies (second antibodies) that are reactive with the monoclonal antibody, such as antibodies specific for immunoglobulin. Alternatively, the monoclonal antibodies can be directly labeled. A wide variety of labels may be employed, such as radionuclides, fluorescers, enzymes, enzyme substrates, enzyme cofactors, enzyme inhibitors, ligands (particularly haptens), etc. Numerous types of immunoassays are available and, by way of example, some include those described in U.S. Pat. Nos. 3,817,827; 3,850,752; 3,901,654; 3,935,074; 3,984,533; 3,996,345; 4,034,074; and 4,098,876, all of which are incorporated herein by reference.

Commonly, the monoclonal antibodies and peptides of the present invention are utilized in enzyme immunoassays, where, for example, the subject antibodies, or second antibodies from a different species, are conjugated to an enzyme. When a biological sample containing HIV antigens, such as human blood serum, saliva, semen, vaginal secretions or viral infected cell culture suspension, is combined with the subject antibodies, binding occurs between the antibodies and those molecules exhibiting the desired epitope. Such proteins or viral particles may then be separated from the unbound reagents, and a second antibody (labeled with an enzyme) added. Thereafter, the presence of the antibody-enzyme conjugate specifically bound to the antigen is determined. Other conventional techniques well known to those skilled in the art may also be utilized.

Kits can also be supplied for use with the subject antibodies in the detection of HIV infection or for the presence of HIV antigen. Thus, the subject monoclonal antibody compositions of the present invention may be provided, usually in a lyophilized form, either alone or in conjunction with additional antibodies specific for other epitopes of HIV. The antibodies, which may be conjugated to a label or unconjugated, are included in the kits with buffers, such as Tris, phosphate, carbonate, etc., stabilizers, biocides, inert proteins, e.g., bovine serum albumin, or the like. Generally, these materials will be present in less than about 5% wt. based on the amount of active antibody, and usually present in total amount of at least about 0.001% wt. based again on the antibody concentration. Frequently, it will be desirable to include an inert extender or excipient to dilute the active ingredients, where the excipient may be present in from about 1% to 99% wt. of the total composition. Where a second antibody capable of binding to the monoclonal antibody is employed, this will usually be present in a separate vial. The second antibody is typically conjugated to a label and formulated in an analogous manner with the antibody formulations described above.

The detection of gp110 or p25 antigens, or the whole virus, in various biological samples may find use in diagnosing a current infection by the HIV virus. Biological samples can include, but are not limited to, blood serum, saliva, semen, tissue biopsy samples (brain, skin, lymph nodes, spleen, etc.), cell culture supernatants, disrupted eukaryotic and bacterial expression systems and the like. Presence of virus is tested for by incubating the monoclonal antibody with the biological sample under conditions conducive to immune complex formation, followed by the detection of complex formation. In one embodiment, complex formation is detected through use of a second antibody capable of binding to the monoclonal antibody which is typically conjugated to a label and formulated in an analogous manner with the antibody formulations described above. In another embodiment, the monoclonal antibody is attached to a solid phase support which is then contacted with a biological sample. Following an incubation step labeled monoclonal antibody is added to detect the bound antigen.

Preparation and Use of Synthetic Peptides

Novel peptides are provided in the present invention which immunologically mimic protein epitopes encoded by the HIV retrovirus, particularly epitopes encoded within the env or gag regions of the viral genome encoding the gp110 or p25, respectively. To accommodate strain-to-strain variations among different isolates, adjustments for conservative substitutions, and selection among the alternatives where non-conservative substitutions are involved, may be made. These peptides can be used as immunogens, to inhibit or eliminate HIV antigen production in vitro or in vivo, for the detection of the virus or of antibodies to the virus in a physiological sample. Depending upon the nature of the protocol, the peptides may be conjugated to a carrier or other compounds, labeled or unlabeled, bound to a solid surface, or the like.

In one embodiment, peptides of interest will be derived from the gp110 region of the virus. Of particular interest is the region within the env open reading frame extending from about base pair (bp) 6688 to about bp6750 and from about bp7246 to about 7317.

The peptides of interest will include at least five, sometimes six, sometimes eight, sometimes twelve, sometimes 21, usually fewer than about 50, more usually fewer than about 35, and preferably fewer than about 25 amino acids included within a sequence coded for by an HIV retrovirus. Desirably, the peptide will be as small as possible while still maintaining substantially all of the immunoreactivity or antiviral activity of the larger peptide. In some instances it may be desirable to join two or more oligopeptides which are non-overlapping to form a single peptide structure or to use them as individual peptides at the same time, which separately or together provide equivalent sensitivity to the parent.

The peptide may be modified by introducing conservative or non-conservative substitutions in the peptide, usually fewer than 20 number percent, more usually fewer than 10 number percent of the amino acids being exchanged. In those situations where regions are found to be polymorphic, it may be desirable to vary one or more particular amino acids to more effectively mimic the differing epitopes of the different retroviral strains. In many instances to provide chemical stability, methionine may be replaced by norleucine (Nor).

It should be understood that the polypeptide employed in the subject invention need not be identical to any particular HIV polypeptide sequence, so long as the subject compound is able to provide for immunological competition with proteins of at least one of the strains of the HIV retrovirus. Therefore, the subject polypeptide may be subject to various changes, such as insertions, deletions, and substitutions, either conservative or non-conservative, where such changes might provide for certain advantages in their use. By conservative substitutions is intended substitutions within groups such as gly, ala; val, ile, leu; asp, glu; asn, gln; ser, thr; lys, arg; phe, tyr; and nor, met. Usually, the sequence will not differ by more than 20% from the sequence of at least one strain of an HIV retrovirus except where additional amino acids may be added at either terminus for the purpose of providing an "arm" by which the peptide of this invention may be conveniently immobilized. The arms will usually be at least 1 amino acid and may be 50 or more amino acids, more often 1 to 10 amino acids, in length.

The peptide in which the amino acid sequence is modified by the substitution, addition or deletion of amino acid residues should retain substantially all of the immunoreactivity or antiviral activity of the unmodified peptides, which may be conveniently measured by various assay techniques disclosed herein.

In addition, one, two, or more amino acids may be added to the termini of an oligopeptide or peptide to provide for ease of linking peptides one to another, for coupling to a support or larger peptide, for reasons to be discussed subsequently, for modifying the physical or chemical properties of the peptide or oligopeptide, or the like.

Amino acids such as tyrosine, cysteine, lysine, glutamic or aspartic acid, or the like may be introduced at the C-or N-terminus of the peptide or oligopeptide to provide for a useful functionality for linking. Cysteine is particularly preferred to facilitate covalent coupling to other peptides or to form polymers by oxidation.

Additionally, the peptide or oligopeptide sequences may differ from the natural sequence by the sequence being modified by terminal- $NH_2$ acylation, e.g., acetylation, or thioglycolic acid amidation, terminalcarboxy amidation, e.g., with ammonia or methylamine, to provide stability, increased hydrophobicity for linking or binding to a support or other molecule, or for polymerization.

Thus, for example, in the peptides I–VIII disclosed above, when Y or Y' are present, a preferred embodiment exists when Y or Y' comprises one or more cysteine residues or a combination of one or more cysteine residues with spacer amino acids. Glycine is a particularly preferred spacer. Preferred peptides for use in oxidative polymerization are those in which Y or Y' represents at least two cysteine residues. When two cysteine residues are present at the same end of the peptide, a preferred embodiment exists when the cysteine residues are separated by from one to three spacer amino acid residues, preferably glycine. The presence of cysteine residues may allow the formation of dimers of the peptide and/or increase the hydrophobicity of the resulting peptide which facilitates immobilization of the peptide in solid phase or immobilized assay systems.

Of particular interest is the use of the mercaptan group of cysteines or thioglycolic acids used for acylating terminal amino groups or the like for linking two of the peptides or oligopeptides or combinations thereof by a disulfide linkage or a longer linkage to form polymers that contain a number of epitopes. Such polymers have the advantage of increased immunological reaction. Where different peptides are used to make up the polymer, they possess the additional ability to induce antibodies that immunoreact with several antigenic determinants of different HIV isolates.

To achieve the formation of antigenic polymers (synthetic multimers), compounds may be employed having bis-haloacetyl groups, nitroarylhalides, or the like, where the reagents are specific for thio groups. Thus, the linking between the two mercapto groups of the different peptides or oligopeptides may be a single bond or a linking group of at least 2, usually at least 4, and not more than about 16, usually not more than about 14 carbon atoms.

The subject peptide may be employed linked to a soluble macromolecular (e.g., not less than 5 kDal) carrier. Conveniently, the carrier may be a poly(amino acid), either naturally occurring or synthetic, to which antibodies are unlikely to be encountered in human serum. Exemplary of such carriers are poly-L-lysine, keyhole limpet hemocyanin, thyroglobulin, albumins, such as bovine serum albumin, tetanus toxoid, etc. The choice of the carrier is primarily dependent upon the ultimate use intended for the antigen, and one of convenience and availability.

With such conjugates, there will be at least one molecule of at least one subject peptide per macromolecule and not more than about 1 per 0.5 kDal, usually not more than about 1 per 2 kDal of the macromolecule. One or more different peptides may be linked to the same macromolecule.

The manner of linking is conventional, employing such reagents as p-maleimidobenzoic acid, p-methyldithiobenzoic acid, maleic acid anhydride, succinic acid anhydride, glutaraldehyde, etc. The linkage may occur at the N-terminus, C-terminus or at a site intermediate to the ends of the molecule. The subject peptide may be derivatized by linking, may be linked while bound to a support, or the like.

Various assay protocols familiar to those skilled in the art may be employed for detecting the presence of either antibodies to retroviral proteins or retroviral proteins themselves. Of particular interest is using the peptide as the labeled reagent, where the label allows for a detectable signal, or binding the peptide, either directly or indirectly to a surface, where antibody to the peptide in the sample will become bound to the peptide on the surface. The presence of human antibody bound to the peptide can then be detected by employing a xenogeneic antibody specific for human immunoglobulin, normally both human IgM and IgG, or a labeled protein specific for immune complexes, e.g., Rf factor of *S. aureus* protein A.

Illustrative of an assay technique is the use of sample container, e.g., wells of microwell plates, where the subject polypeptide or conjugates thereof are adsorbed to the container bottom and/or walls either covalently or non-covalently. The sample, normally human blood or serum diluted in appropriately buffered medium, is added to the container and a sufficient time allowed for complex formation between the polypeptide(s) and any cognate antibodies in the sample. The supernatant is removed and the container washed to remove non-specifically bound proteins. A labeled specific binding protein which specifically binds to the complex, such as xenogeneic antiserum to human immunoglobulin, is employed for detection.

The peptide can be prepared in a wide variety of ways. The peptide, because of its relatively short size, may be synthesized in solution or on a solid support in accordance with conventional techniques. Various automatic synthesizers are commercially available today and can be used in accordance with known protocols. See, for example, Stewart and Young, Solid Phase Peptide Synthesis, 2nd ed., Pierce Chemical Co., 1984; and Tam et al., *J. Am Chem. Soc.* (1983) 105:6442.

Alternatively, hybrid DNA technology may be employed where a synthetic gene may be prepared by employing single strands which code for the polypeptide or substantially complementary strands thereof, where the single strands overlap and can be brought together in an annealing medium so as to hybridize. The hybridized strands may then be ligated to form the complete gene, and, by choice of appropriate termini, the gene may be inserted into expression vectors, which are readily available today. See, for example, Maniatis et al., Molecular Cloning, A Laboratory Manual, CSH, Cold Spring Harbor Laboratory, 1982. Or, the region of the viral genome coding for the peptide may be cloned by conventional recombinant DNA techniques and expressed (See, Maniatis, supra).

DNA coding sequences from the $LAV_{BRU}$ and ARV 2 isolates of HIV which may be used for expressing the peptides include the following:

| | | | | | | | | | | | |
|---|---|---|---|---|---|---|---|---|---|---|---|
| $LAV_{BRU}$ | TGT | ACA | AGA | CCC | AAC | AAC | AAT | ACA | AGA | AAA | AGT |
| | ATC | CGT | ATC | CAG | AGG | GGA | CCA | GGG | AGA | GCA | TTT |
| | GTT | ACA | ATA | GGA | AAA | ATA | GGA | AAT | ATG | AGA | CAA |
| | GCA | CAT | TGT | | | | | | | | |
| ARV-2 | TGT | ACA | AGA | CCC | AAC | AAC | AAT | ACA | AGA | AAA | AGT |
| | ATC | TAT | ATA | GGA | CCA | GGG | AGA | GLA | TTT | CAT | ACA |
| | ACA | GGA | AGA | ATA | ATA | GGA | GAT | ATA | AGA | AAA | GCA |
| | CAT | TGT | | | | | | | | | |

Fragments from a sequence may be employed for expression of peptide fragments, conservative base changes can be made, where the modified codon(s) code for the same amino acid(s), or non-conservative changes in the coding sequence may be made, where the resulting amino acid may be a conservative or non-conservative change in the amino acid sequence, which was discussed previously.

The coding sequence may be extended at either the 5′- or 3′-terminus or both termini to extend the peptide, while retaining its epitopic site(s). The extension may provide for an arm for linking, e.g., to a label, such as an enzyme, for joining two or all of the peptides together in the same chain, for providing antigenic activity, convenient restriction sites for cloning, or the like.

The DNA sequence by itself, fragments thereof, or larger sequences, usually at least 15 bases, preferably at least 18 bases, may be used as nucleotide probes for detection of retroviral RNA or proviral DNA, or for identifying homologous regions for cloning or sequencing. Numerous techniques are described, such as the Grunstein-Hogness technique, Southern technique, Northern technique, dot-blot, improvements thereon, as well as other methodology, such as disclosed in U.S. Pat. No. 4,358,535, which is incorporated herein by reference.

The subject peptides and their analogs find use by themselves or in combination in vaccines. Similarly, anti-idiotype antibodies, i.e., reactive with the idiotypes of the antibodies of the present invention and thereby containing epitopes mimicking neutralizing regions of HIV, may also be used in vaccines. The peptides or anti-idiotype antibodies may be formulated in a convenient manner, generally at concentrations in the range of 1 ug to 20 mg/kg of host. Physiologically acceptable media may be used as carriers, such as sterile water, saline, phosphate buffered saline, and the like. Adjuvants may be employed, such as aluminum hydroxide gel, surface active substances such as lysolecithin, pluronic polyols, polyanions, peptides, proteins (e.g., diptheria or cholera toxin) and oil emulsions. The peptides may also be incorporated into liposomes, or conjugated to polysaccharides, polypeptides or polymers for use in vaccine formulation. Administration may be injection, e.g., intramuscularly, peritoneally, subcutaneously, intravenously, etc. Administration of an immunogenically effective dose may be one or a plurality of times, usually at one to four week intervals. An "immunogenically effective dose" is that amount of a vaccine suitable to elicit an immune response in a host, whereby the host demonstrates increased infection.

Other features and advantages of the present invention will become apparent from the following experimental descriptions, which describe the invention by way of example. The examples are offered by way of illustration and not by way of limitation.

EXAMPLE I

Generation and Characterization of Monoclonal Antibodies

Example I describes the generation of hybrid cell lines which produce monoclonal antibodies specific for the envelope glycoproteins of HIV. This method involves the use of lectin purified extracts of $LAV_{BRU}$ attached to lentil lectin agarose as the immunogen. The monoclonal antibodies subsequently generated by the hybrid cell lines are characterized by their ability to immunoblot and radioimmune precipitate gp110 from purified LAV and as biologically-expressed recombinant fusion protein. The monoclonal antibodies that bind to epitopes on gp110 are also reactive in ELISAs with disrupted whole virus, fusion proteins and synthetic peptides, and react with whole virus in indirect fluorescent assays.

The protocols for the generation of the hybrid cell lines producing monoclonal antibody and the characterization of the antibodies were as follows.

LAV virus purified from infected CEM cells (A.T.T.C. No. CRL8904) was disrupted in 50 mM Tris, pH 7.4, 0.15 M NaCl, 1.0% Aprotinin, 2.0% Nonidet P-40(®) (NP-40) (octylphenoxypolyethoxyethanol). The extract was clarified twice by centrifugation and adjusted to 0.5% NP-40 with the addition of three volumes of disruption buffer without NP-40. Lentil lectin Sepharose (Pharmacia, Piscataway, N.J.) was prewashed in disruption buffer without NP-40 and then equilibrated in adsorption buffer (50 mM Tris, pH 7.4, 0.15 M NaCl, 1.0% Aprotinin, 0.5% NP-40). Clarified viral extract was adsorbed with lentil lectin Sepharose for 42 h at 4° C. Unadsorbed material was removed by washing with excess adsorption buffer. Elution of adsorbed material was carried out with 0.2 M alpha methyl mannoside in adsorption buffer. The eluent was dialyzed against PBS to remove the sugar and the material was readsorbed to the lentil lectin Sepharose.

The glycoprotein-lentil lectin Sepharose complex was used to immunize BALB/c mice by three intraperitioneal injections without adjuvant given 2-3 weeks apart. Spleens were removed from immunized mice which demonstrated circulating antibody to glycoproteins of HIV by immunoblot, RIP and/or ELISA.

Protocols used for the generation of cell lines were generally those of Kohler and Milstein (*Nature* 256:495 (1985)) with the modifications of Goldstein, L. C., et al., (*Infect. Immun.* 38:273 (1982)). Splenic B-lymphocytes from the immunized mice were fused with NS-1 myeloma cells using 40% (w/v) polyethylene glycol. Following fusion the cell mixture was resuspended in HAT medium (RPMI—1640 medium supplemented with 15% fetal calf serum, $1\times10^{-4}$ M hypoxanthine, $4\times10^{-7}$ M aminopterin and $1.6\times10^{-5}$ M thymidine) to select for the growth of hybrid cells, and then dispensed into 96-well microculture trays at a concentration of 1 to $3\times10^6$ cells/ml and incubated at 37° C. in a humidified atmosphere containing 6% $CO_2$. Cultures were fed by replacement of one-half the supernatant with fresh HAT medium. The wells were observed using an inverted microscope for signs of cell proliferation and when the cells were of sufficient density the supernatants were tested for anti-LAV antibody.

Wells containing hybrid cells producing antibody to LAV were identified by ELISAs measuring the binding to either purified whole disrupted virus or biologically-expressed fusion proteins. ELISA assays using disrupted virus were carried out on LAV EIA plates (Genetic Systems, Seattle, Washington). Plates were incubated with cell culture fluids at 37° C. for 45 minutes and then washed three times with 0.05% Tween 20 in phosphate buffered saline (PBS-Tween).

Peroxidase-goat anti-mouse IgG (1:2,000 dilution in PBS-Tween; Zymed Laboratories, Inc., South San Francisco, Calif.) was added (100 ul per well), and the plates were incubated for 45 minutes at 37° C. and washed as above. Substrate (0.025 M citric acid, 0.05 M dibasic sodium phosphate, pH 5.0 containing 14 mg of o-phenylenediamine and 10 ul of 30% hydrogen peroxide per 50 ml) was added and the plates were incubated for 30 min at room temperature in the dark. The reaction was stopped with 3N sulfuric acid, and colorimetric reactions were quantitated with an automated microplate reader. Wells that gave positive results were subcloned by limiting dilution, retested for specificity, then expanded.

The monoclonal antibodies secreted by the resulting hybrid cell lines were further characterized as to specificity and reactivity by immunoblotting, immunoprecipitation and ELISA using disrupted LAV virus, recombinant LAV fusion proteins and synthetic LAV peptides. All antibodies were determined to be of the $IgG_1$ isotype. Cell lines HIV-gp110-1, HIV-gp110-2, HIV-gp110-4, HIV-gp110-5, and HIV-gp110-6 HIV-gp110-3 have been deposited with the American Type Culture Collection prior to the filing of this application and designated A.T.C.C. Nos. HB 9175, HB 9176, HB 9405, HB 9406, and HB 9404 HB 9177, respectively.

Recombinant fusion proteins tested for reactivity have previously been designated ENV2, ENV3, ENV4 and ENV5. Protein ENV2 is expressed from pENV2 (A.T.C.C. No. 53071), which is a region of LAV from base pair (bp) 6598 through bp 7178 (numbering according to Wain-Hobson et al., Cell 44:9 (1985)), ENV3 is expressed from pENV3 (A.T.C.C. No. 53072), which comprises the LAV region from bp 7178 through bp 7698; ENV4 is expressed from pENV4 (A.T.C.C. No. 53073), and comprises bp 7698 through bp 8572; and ENV5 is expressed from pENV5 (A.T.C.C. No. 53074), which comprises the LAV region bp 5889 through bp 7698. The production of the recombinant fusion proteins is described in detail in commonly-owned pending U.S. patent application, Ser. No. 721,237, which is incorporated herein by reference.

Assembly of Synthetic Peptides

Peptides I (29) and VIII (110-2-2) were assembled on a benzhydrylamine (polystyrene/divinylbenzene) resin (Applied Biosystems, Inc., Foster City, Calif.). Peptide V (177) was assembled on a t-butyloxycarbonyl(Boc)-ethylbenzylcysteine-phenylacetamidomethyl (PAM) polystyrene/divinylbenzene resin. Symmetrical anhydride couplings were carried out in an Applied Biosystems 430A synthesizer. Cysteine was added as the first residue in both peptides.

Dicyclohexylcarbodiimide couplings in the presence of hydroxylbenzotriazole were used for asparagine and glutamine. Benzy-based side chain protection and Boc alpha-amine protection were used. Other side chain protection routinely used was Boc (formyl) tryptophan, Boc methionine sulfoxide, Boc (tosyl) arginine, Boc (methylbenzyl) cysteine Boc (tosyl) histidine, Boc (chlorobenzyloxycarbonyl) lysine and Boc (bromobenzyloxycarbonyl) tyrosine.

When the peptides were radiolabeled, it was by acetylating the amino terminus with $^3$H-acetic acid and an excess of dicyclohexylcarbodiimide.

Deprotection and cleavage of the peptide from the resin was by the Tam "low-high" HF protocol (Tam et al., supra). Extraction from the resin was with 5% acetic acid and the extract was subjected to gel filtration chromatography in 5% acetic acid.

Synthetic HIV peptides tested for reactivity with the monoclonal antibodies included peptides 29, 36, and 39. Peptide 29 is encoded by the $LAV_{BRU}$ genomic region from about bp 6688 through bp 6750; peptide 36 is encoded by the region from about bp 7246 through bp 7317; and peptide 39 is encoded by the region from about bp 7516 through bp 7593. Peptides 36 and 39 are described in detail in U.S. Pat. No. 4,629,783, which is incorporated herein by reference.

Immunoblotting

Characterization by immunoblotting was carried out on clone supernatants or ascites fluid using purified LAV virus and recombinant fusion proteins as antigens. The antigens were first separated by polyacrylamide gradient gel electrophoresis (7.0–15.0%) and transferred to nitrocellulose membrane (NCM) by electrophoresis for four hours at 25 V in 25 mM sodium phosphate (pH 7.0). After transfer, the NCM was blocked to prevent nonspecific interactions by incubation in PBS-Tween or Blotto (5% non-fat dry milk in PBS) for one hour at room temperature. The NCM was incubated with cell culture supernatant or ascites fluid diluted in PBS-Tween for one hour at room temperature and was rinsed with three changes of PBS-Tween. In the second step the NCM was incubated with goat anti-mouse IgG-horseradish peroxidase diluted in PBS-Tween for one hour at room temperature. This incubation was followed by washing with PBS-Tween and then immersion in horseradish peroxidase color development solution (Bio-Rad Laboratories, Richmond, Calif.) for 20 minutes. The reaction was stopped by immersion in deionized water. Monoclonal antibody reactivity was compared to a positive control serum reactive with purified disrupted virus or expressed fusion protein. The results showed that all antibodies bound to gp110 and its precursor molecule, gp150, using disrupted virus preparations. Antibodies 110-1 and 110-2 also recognized the fusion protein ENV3, whereas antibodies 110-3, 110-4, 110-5, and 110-6 immunocomplexed ENV2.

Immunoprecipitation

Viral extracts for radioimmune precipitation were prepared from CEM cells infected with the LAV$_{BRU}$ isolate of HIV adapted to lytic growth by continuous passage. When early cytopathic effects were evident, the cells were transferred to labeling media containing $^{35}$[S]-methionine (0.05 mCi/ml) or $^{3}$[H]-glucosamine (0.025 mCi/ml), then incubated for 24 h until most of the cells had lysed, releasing virus into the culture supernatant. Virus was pelleted (one hour at 100,000 xg) from the cell-free supernatant, and detergent extracts were prepared in P-RIPA buffer (phosphate buffered saline containing 1.0% Triton X-100, 1.0% deoxycholate, 0.1% SDS, and 1% Aprotinin). Similar extracts were prepared from the supernatants of uninfected CEM cells.

Immunoprecipitation assays were performed with 100 ul of virus extract incubated with 100 ul culture supernatant from the hybrid cell lines for one hour on ice. Four microliters of rabbit anti-mouse Ig (Zymed Laboratories, So. San Francisco, Calif.) was added to each sample and incubated 30 minutes. Immunoprecipitin (100 ul; Bethesda Research Laboratory, Bethesda, Md.) resuspended in P-RIPA buffer containing 1.0% ovalbumin was added to each sample and incubated for an additional 30 minutes. The bound complexes were washed and separated by SDS-polyacrylamide gel electrophoresis (15.0% acrylamide: DATD gel). Following electrophoresis the gels were fixed, soaked in Enhance (New England Nuclear, Boston, Mass.), dried and exposed to Kodak XR-5 film. A reference positive serum which immunoprecipitated all HIV viral proteins was reacted with viral-infected and mock-infected CEM cell supernatants as positive and negative controls.

The results showed that all six monoclonal antibodies specifically immunoprecipitated gp110 and gp150.

Enzyme-Linked Immunoadsorbant Assay

To map the gp110 epitopes being recognized by the monoclonal antibodies of the present invention, culture supernatants from hybrid cell lines or ascites fluid were further characterized by reactivity in ELISAs with biologically-expressed fusion proteins and synthetic peptides. Procedures were the same as those described above with the exception that fusion proteins or synthetic peptides replaced purified virus as the antigen adsorbed to the surface of the microtiter wells.

When peptides were used as antigen the plating protocol was as follows. Lyophilized peptide was dissolved in 6 M guanidine HCl. Just prior to plating in the 96 well plates, the guanidine solution was diluted into 0.05 M carbonate/bicarbonate buffer (pH 9.6) to a final peptide concentration of up to 100 ug/ml. A 50 ul volume of the diluted peptide was placed in each microtiter well and the plates were then incubated overnight at 4° C. Excess peptide solution was "shaken out", plates were blocked with Blotto, and the procedure described above was followed for the rest of the ELISA. Similarly, recombinant protein was diluted to a final concentration of about 2 ug/ml in 0.05 M carbonate/bicarbonate buffer (pH 9.6) before the same procedure was followed.

The results are shown in Table II. Monoclonal antibodies produced by cell lines HIV gp110-1 and HIV gp110-2 reacted with ENV3, ENV5, peptide 36 and disrupted virus. Antibodies from cell lines HIV-gp110-3, HIV-gp-110-4, HIV-gp110-5 and HIV-gp110-6 reacted with ENV2 and peptide 29 as well as disrupted virus.

TABLE II

ELISAs Showing Reactivity of Monoclonal Antibodies With Recombinant Proteins and Synthetic Peptides

| | Recombinant Fusion Protein | | | | Synthetic Peptide | | | LAV | CEM |
|---|---|---|---|---|---|---|---|---|---|
| | ENV2 | ENV3 | ENV4 | ENV5 | 29 | 36 | 39 | Control | Control |
| 110-1 | 0.077 | 3.000 | 0.113 | 3.000 | ND | 2.421 | 0.054 | 0.908 | 0.125 |
| 110-2 | −0.003 | 3.000 | 0.000 | 3.000 | ND | 2.305 | −0.005 | 1.214 | 0.009 |
| 110-3 | 3.000 | 0.011 | ND | ND | 3.000 | ND | 0.017 | 0.363 | 0.046 |
| 110-4 | 3.000 | 0.020 | ND | ND | 3.000 | ND | 0.016 | 0.383 | 0.067 |
| 110-5 | 3.000 | 0.014 | ND | ND | 3.000 | ND | 0.016 | 0.368 | 0.025 |
| 110-6 | 3.000 | 0.033 | ND | ND | 1.937 | ND | 0.017 | 0.486 | 0.032 |

The results in Table II demonstrated that monoclonal antibodies 110-1 and 110-2 recognized an antigenic determinant encoded by a DNA sequence within the pENV3 region, more particularly by the region of the HIV genome defined by a sequence of amino acids within peptide 36. That is, monoclonal antibodies gp110-1 and 110-2 bind to a peptide region of gp110 encoded within bp7246 through 7317, as evidenced by the formation of immune complexes with peptide 36 and ENV3. This region of the HIV genome has previously been identified as conserved, i.e., little change in the DNA sequence in the region encoded by peptide 36 among different viral isolates from diverse geographical locations. See Starcich et al., Cell 46:637 (1986). In contrast, monoclonal antibodies gp110-3, -4, -5, and -6 bind to peptides of HIV defined by the region encoded by peptide 29 from bp 6688 through about bp 6750. The region in gp110 defined by peptide 29 has been identified as containing several nucleotide substitutions among different viral isolates. Monoclonal antibodies that selectively bind gp110 polypeptides which contain conserved epitopes, such as antibodies 110-1 and 110-2, may have enhanced utility in a variety of circumstances, such as in affinity chromatography, etc. Also, in an ELISA assay, the peptide 110-2-2 reacted with sera from the individual from whom LAV-2 was isolated.

Indirect Immunofluorescent Assay

Indirect immunofluorescent assays using monoclonal antibodies directed against the gp110 antigen of HIV were carried out on acetone-fixed and live cells. Acetone-fixed slides prepared from LAV-infected CEM cells were incubated with diluted culture supernatant or ascites fluid for one hour at 37° C., while live cells were incubated with culture supernatant or ascites fluid for one hour at 4° C. before the cells were placed on slides and acetone fixed. Both methods used fluorescein isothiocyanate-labeled anti mouse IgG to detect cells bearing the reactive gp110 antigen. Monoclonal antibody HIV-gp110-1 gave positive results using either live or acetone-fixed LAV-infected cells.

EXAMPLE II

Neutralization of HIV Infectivity by Anti-gp110 Monoclonal Antibodies

This example describes and characterizes the neutralization of HIV infectivity using monoclonal antibodies which bind to gp110 and peptides within gp110. The results indicate that monoclonal antibodies gp110-3, -4, -5 and -6 possess neutralizing activity, and that gp110-3 and -4 possess particularly high levels of neutralizing activity.

Neutralization Assay

A sensitive neutralization assay was developed to quantitate the effect of the monoclonal antibodies on HIV infectivity. A CD4+cell line highly susceptible to HIV infection, CEM, was chosen as a target cell for infectivity comparisons. Ascites fluid prepared as described in Example I, or the IgG fraction thereof purified using ammonium sulfate precipitation, was heat inactivated at 56° C. for 30 minutes, then diluted as required in RPMI medium containing 10% fetal calf serum. A suspension of HIV strain LAV-$_{BRU}$ was harvested from about four-day cultures of CEM in log growth phase, filtered through 0.2 or 0.45 micron filters, aliquoted, and frozen at −70° C. One aliquo was thawed, titrated to determine the TCID$_{50}$, and subsequent assays performed with freshly thawed aliquots, diluted 1:500 in culture medium to a concentration of approximately ten times the amount required to infect 50% of CEM cells in culture (10 TCID$_{50}$). The virus suspension was mixed with an equal volume (250 ul) of monoclonal antibody preparation of five-fold dilutions from 1:5 to 1:9,765,625. The virus/antibody mixture was incubated for 45 minutes at 37° C. and then duplicate samples of 200 ul used to inoculate wells containing 1.0 ml of approximately 2×10$^5$ CEM cells per well. The cultures were incubated 37° C. in a humidified, 5% CO$_2$ atmosphere for 14 days. The cells were harvested, pelleted, and lysed with 1% Triton X-100 in PBS for about 10 minutes. The amount of virus (or viral antigen) present in lysed cells was quantitated using a sensitive HIV antigen capture "sandwich" enzyme immunoassay described below. The titer of neutralizing activity, if any, was determined as the reciprocal of the dilution of monoclonal antibody which inhibited antigen production by greater than 50% of virus control cultures incubated without antibody, or with a monoclonal antibody of the same isotype which had previously been shown to lack neutralizing activity.

The HIV antigenic capture assay referred to above employed two monoclonal antibodies directed against p25 antigens as capture reagents. These hybridoma cell lines were generated by the methods described above with minor modifications, including using a purified gag recombinant fusion protein as the immunogen and characterizing the resultant monoclonal antibodies as to specificity and reactivity using recombinant fusion proteins previously designated GAG-1, GAG-2, and GAG-3, and the synthetic peptide 141. Protein GAG-1 is expressed from pGAG-1 (A.T.C.C. No. 53379), GAG-2 is expressed from pGAG-2 (A.T.C.C. No. 53111) and GAG-3 is expressed from pGAG-3 (A.T.C.C. No. 53112). The production of the recombinant fusion proteins is described in detail in commonly owned pending patent application numbers U.S. Ser. Nos. 764,460 and 828,828, which are incorporated herein by reference. Synthetic peptide 141 is encoded by the LAV$_{BRU}$ genomic region corresponding to the amino acid residues 198–242. Monoclonal antibody produced by hybridoma cell lines p25-2 and p25-3 are found to be reactive with recombinant fusion proteins GAG-1, GAG-2, and GAG-3, and the monoclonal of p25-3 also is reactive with synthetic peptide 141.

To perform the antigen capture assay, the capture reagents which were first adsorbed to a solid support. Ascites fluid derived from hybridoma cell lines p25-2 and p25-3 were diluted 1:5000 in 25 mM Tris buffer, pH 8.5 and 200 ul was placed into wells of microwell plates. Wells were sealed and incubated for about 16 hours at 4° C. The solution was removed from the wells by aspiration before a blocking solution of 0.3% Blotto in PBS was added. Blocking was carried out for 15 minutes at room temperature. The blocking solution was aspirated and the sample was added. Two hundred microliters of the lysed cellular suspension and 5.0 ul of detection conjugate, prepared as described below, were added to each well. The well strips or plates were incubated for 2 h at 37° C., after which the suspension was aspirated and the wells washed four times with buffer (0.05% Tween 20 in PBS). The detection conjugate was prepared as follows. Monoclonal antibodies p25-6 and p25-7 were conjugated to horseradish peroxidase (HRP) at a 3:1 molar ratio (Ab:HRP) for three hours using a periodate oxidation procedure (Nakane, et al., J. Histochem. Cytochem. 22:1084 (1974)). Conjugates were diluted 1:1500 in 2.5% (w/v) non-fat dry milk, 0.01% thimerosal, and 0.005% Antifoam A in 20 mM sodium citrate. The remainder of the ELISA procedure was performed as described in Example I.

The results of the assay of neutralizing activity with antibodies gp110-3, -4, -5, and -6 are as follows. The highest titers which retained neutralizing activity were determined to be: gp110-3=15,625; gp110-4=9,765,625; gp110-5=125; and gp110-6=625.

Due to the predicted genetic variability of the region defined by peptide 29, the ability of monoclonal antibody gp110-4 to recognize other isolates of HIV was examined. The immunofluorescence assays were performed as described above. Antibody gp110-4 detected antigen in cultures of at least 3 of 16 HIV isolates tested.

Antibody gp110-4 was able to neutralize viruses isolated over fifteen weeks from a chimpanzee inoculated with LAV$_{BRU}$ as a control animal in an AIDS vaccine trial. The monoclonal antibody was able to neutralize the isolates even though the animal had serum antibodies which neutralized HIV in vitro, and had developed a measurable cell mediated immune response to the HIV infection. This indicates a lack of antigenic drift in vivo for the epitope recognized by the gp110-4 antibody.

EXAMPLE III

Neutralization of HIV Infectivity by a Cocktail of Anti-gp110 and Anti-p25 Monoclonal Antibodies This example describes the neutralization of HIV infectivity using monoclonal antibodies which bind to gp110 and peptides within gp110 in combination with monoclonal antibodies which bind to p25 and peptides within p25, which alone show little or no neutralizing activity. The results indicate that monoclonal antibody gp110-2 in combination with either p25-6 or p25-7 possesses particularly high levels of neutralizing activity.

Hybridoma cell lines p25-6 and p25-7 were generated by the methods described above with modifications which include using inactivated disrupted virus or a purified gag recombinant fusion protein expressed in *E. coli* as the immunogen, and characterizing the resultant monoclonal antibodies as to specificity and reactivity using the recombinant fusion proteins previously designated GAG-1, GAG-2, and GAG-3 and the synthetic peptides 15, 88, 150, 147, and 148. The synthetic peptides are encoded by the LAV$_{BRU}$ genomic region corresponding to amino acid residues as follows: peptide 15, amino acid residues 329 through 350; peptide 88, amino acid residues 315 through 350; peptide 150, amino acid residues 318 through 363; peptide 147, amino acid residues 278 through 319; and peptide 148, amino acid residues 290 through 319. Monoclonal antibodies produced by hybridoma cell lines p25-6 and p25-7 are reactive with the recombinant fusion protein GAG-3, p25-6 is reactive with synthetic peptides 147 and 148, and p25-7 is reactive with synthetic peptides 15, 88, and 150.

Neutralization assays were carried out as described above, except when cocktails were used, individual monoclonal antibodies were first diluted 1:5 in culture medium and then mixed in equal ratios to yield a final dilution of 1:10. The remainder of the assay was carried out as described above.

Monoclonal antibodies gp110-2, p25-6 and p25-7 show less than 50% neutralizing activity when used alone. When used in a cocktail which includes monoclonal antibodies gp110-2 with p25-6 or gp110-2 with p25-7 at a 1:10 dilution, there was total neutralization. A cocktail including the monoclonal antibodies p25-6 in combination with p25-7 gave neutralizing activity range of 60-90%.

EXAMPLE IV

Immunopotency of Peptide 29 and Homologs

The ability of peptide 29 and homologous peptides, including peptide 177, to stimulate an immune response against HIV is first examined in two strains of mice. The procedures for the preparation of the peptide immunogens, immunization protocols, and for the characterization of the immune response generated are detailed below.

Peptide 29 is prepared for immunization by conjugation to a purified thyroglobulin. Thyroglobulin may be derivatized with N-succinimidyl-4-(N-maleimidomethyl)cyclohexane-1-carboxylate (SMCC) for conjugation according to the procedure outlined in U.S. Pat. No. 4,629,783, col. 10, lines 28-51. As a second immunogen, thyroglobulin is derivatized with glutaraldehyde as follows. Porcine thyroglobulin, 27 mg, is dissolved in 1 ml of 0.1 M sodium bicarbonate, to which 8.3 ul of a 25% glutaraldehyde solution is added dropwise, and the mixture stirred overnight at room temperature. 1 ml of sodium carbonate/bicarbonate buffer, pH 9.3, is added to the solution and then dialyzed for 8 hours against 2 liters of the same buffer at 4° C., with a complete change of dialysate at 4 hours. Peptide 29 is then added to the derivatized thyroglobulin at approximately 100 molar excess, and the mixture stirred overnight at room temperature. Unreacted glutaraldehyde is blocked with 200 ul of a 0.2 M lysine solution, which mixture is stirred for several hours (or overnight) at room temperature. The peptide-thyroglobulin conjugate is then dialyzed extensively against PBS at 4° C.

Two strains of mice, (C57 black and BALB/c) are inoculated with peptides prepared by each method of conjugation. All animals are about 2-4 weeks old at the time of inoculation. The route of inoculation may be footpad, tail scarification, subcutaneous, intranasal, or intraperitioneal. The inoculum consists of 25 ug of conjugated peptide suspended in 0.5 ml of complete Freund's adjuvant, with booster inoculations repeated at weeks 2, 3 and 5 with the same immunogen suspended in incomplete freund's adjuvant. Serum samples from individual mice are collected prior to immunization, 4 days after the booster immunization at 3 weeks, and 4 days after the final booster at 5 weeks. The serum samples are analyzed for antibodies against homologous peptides or whole virus by screening in ELISAs. The sera demonstrating antibody activity to LAV are further screened for neutralizing activity, followed by analyzing the sera in immunoblots to disrupted LAV antigen and radioimmunoprecipitation assays with radiolabeled gp110.

Serum samples from immunized mice which (i) demonstrate antibodies to whole virus; (ii) are able to neutralize HIV, such as in the assays described in Example II; and (iii) are reactive with peptide 29 in ELISAs, cumulatively indicate the efficacy of the use of peptide 29 in a vaccine formulation.

EXAMPLE V

Immunoaffinity Separation of GP110 Using Monoclonal Antibody

Monoclonal antibodies to the gp110 antigen of HIV can be used in immunoaffinity separation procedures to substantially purify bacterially-expressed recombinant fusion proteins. If the expressed protein is secreted by the bacteria, the protein may be isolated from the culture supernatant; if the protein is not secreted, disruption of the bacterial cells may be necessary.

Construction of plasmid pENV-5 (A.T.C.C. No. 53074) is described in copending commonly-owned patent application U.S. Ser. No. 721,237, which is incorporated herein by reference. Plasmid pENV-5 encodes a major portion of the carboxyl end of gp110 and a portion of the amino terminus of gp41 of LAV inserted into the trp expression vector. *E. coli* C600 transformed by this vector expresses but does not secrete the gp110 fusion protein.

*E. coli* C600 containing the plamid pENV-5 are grown in medium containing tryptophan (20 ug/ml) and ampicillin (100 ug/ml) overnight at 37° C. with aeration. The overnight cultures are then inoculated at 1:100 into fresh minimal medium containing ampicillin (100 ug/ml) but not tryptophan. These cultures are grown with aeration for 2-3 hours (up to early log phase) at 37° C. The inducer, 3-B-indole-acrylic acid (Sigma Chemical Co., St. Louis, Mo.), is added to a final concentration of 20 ug/ml from freshly made stocks of 20 mg/ml in 95% ethanol. Induced cultures are then grown at 37° C. with aeration for 4 to 5 hours and then pelleted and, optionally, frozen. Protein yields from pENV-5 are typically less than 1 mg/liter.

The pelleted bacterial cells are lysed using P-RIPA buffer (PBS containing 1% Triton X-100, 1% deoxycholate, 0.1% sodium dodecyl sulfate, and 1% Aprotinin) which will lyse *E. coli* cells. The suspension can be sonicated to shear DNA and RNA, followed by centrifugation to remove particulates. A dilution or concentration step may then be needed to standardize the protein concentration.

Monoclonal antibody HIV-gp110-1 is precipitated initially from ascites fluid or cell culture supernatants at room temperature or in the cold with $(NH_4)_2SO_4$ or $Na_2SO_4$ solutions buffered at pH 7.3 to final saturation of 33 or 18%, respectively. Precipitated proteins are removed by contrifugation and redissolved in PBS and precipitated a second time with 33% $(NH_4)_2SO_4$ or 12-15% $Na_2SO_4$. This step can be repeated as necessary. The pellet is again dissolved in PBS and the excess salts are removed by gel filtration through a desalting matrix or by exhaustive dialysis against PBS.

Purified 110-1 monoclonal antibody can then be coupled to the cyanogen bromide-activated Sepharose. The necessary amount of gel is swollen in $10^{-3}$ M HCl solution on a glass filter (1 g of freeze-dried material yields a final gel volume of approximately 3.5 ml) and washed for 15 minutes with the same solution, and the antibody added immediately thereafter. In general, the coupling reaction proceeds most efficiently in a pH range 8-10, but a lower pH can be used if needed for antibody stability. The antibody should be dissolved in PBS, or a high ionic strength carbonate/bicarbonate or borate buffer with 150 mM NaCl. The activated Sepharose and antibody suspension is stirred gently for 2-4 hours at room temperature, or overnight at 4° C., and then washed on a course fritted glass filter with coupling buffer. Any remaining active groups are blocked by treatment with 1.0 M ethanolamine at pH 8 for 2 hours. The final antibody-Sepharose product is then washed alternately with high and low pH buffer solutions (borate buffer, 0.1 M, pH 8.5, 1 M NaCl and acetate buffer, 0.1 M, pH 4.0, 1 M NaCl, respectively) four or five times. This washing removes traces of non-covalently adsorbed materials. The finished immunoaffinity separation matrix is stored below 8° C. in the presence of a suitable bacteriostatic agent, such as 0.01% azide.

The addition of the expressed protein suspension to the immunoaffinity separation matrix results in the selective removal of the gp110 antigen. The mixture is allowed to interact for 2-24 hours, preferably 12-18 hours, with slow stirring or rocking. A column format can also be used in which the immunoaffinity matrix is poured into a column, equilibrated, and the expressed protein suspension added slowly to the column. After the protein suspension has been added the flow should be stopped to allow maximum immune complex formation.

Unbound material is washed or separated away by extensive washing with adsorption buffer. A course fritted glass filter with vacuum can be used or column flow-through. The bound material is then eluted using low or high pH buffers (acetate buffer, pH 4.0 or borate buffer, pH 8.56) or a chaotropic agent.

EXAMPLE VI

Immunoaffinity Purification of Recombinant GP110 From a Mammalian Expression System The monoclonal antibodies of the present invention find use in the immunoaffinity purification of recombinant fusion gp110 expressed by mammalian cells. Mammalian cells are infected with recombinant vaccinia (Mackett et al., *J. Virol.* 49:857 (1984), which is incorporated by reference) that contain sequences encoding at least the portion of gp110 which is antigentic and elicits neutralizing antibodies.

The recombinant vaccinia is constructed according to the method described in U.S. Ser. No. 842,984, which is incorporated herein by reference. Briefly, sequences coding for the envelope glycoprotein of HIV are inserted into a plasmid vector (pGS20) downstream from a vaccinia transcriptional control element. This chimeric gene is flanked by sequences encoding the viral thymidine kinase (TK) gene.

Chimeric plasmid vectors containing vaccinia virus promoter ligated to the LAV envelope gene are used to transform *E. coli* strain MC1000. Insertion of the chimeric LAV-env sequences into the vaccinia virus genome was achieved by in vivo recombination, made possible by the fact that the chimeric genes in plasmids pv-env5 are flanked by vaccinia virus sequences coding for the TK gene. This plasmid is then introduced into cells previously infected by wild-type vaccinia virus and recombination allowed to occur between the TK sequences on the plasmid and the homologous sequences in the vaccinia viral genome, thereby inserting the chimeric gene. African Green Monkey kidney cells (strain BSC-40, a line derived from BSC-1 cells, A.T.C.C. No. CCL26) are used as the host in the expression system.

Confluent BSC-40 cells are infected at a multiplicity of infection of 10 by recombinant vaccinia virus. Infection is allowed to proceed for 12 hours, at which time the cells are harvested, washed once with PBS, and collected by centrifugation. Cell pellets are resuspended in lysis buffer (1.0% NP 40, 2.5% sodium deoxycholate, 0.1 M NaCl, 0.01 M M Tris-HCl, pH 7.4, 1 mM EDTA), and the lysate is then cleared by centrifugation. Immunoaffinity separation of the expressed recombinant fusion protein is performed as described above for the bacterial expression system, employing the monoclonal antibody gp110-1. The proteins produced by this expression system more closely resemble naturally produced HIV gp110 because of the processing and glycosylation afforded by the mammalian cells.

From the foregoing, it will be appreciated that the monoclonal antibodies and peptides of the present invention provide improved methods for neutralizing and/or inhibiting HIV infections. This allows prophylactic and therapeutic compositions to be more easily developed that can be effective against infections due to most, if not all, HIV strains. In addition, the novel materials find uses in diagnostic assays and other well-known procedures.

Although the present invention has been described in some detail by way of illustration and example for purposes of clarity of understanding, it will be apparent that certain changes and modifications may be practiced within the scope of the appended claims.

What is claimed is:

1. A cell line that produces a monoclonal antibody which specifically reacts with an epitope of HIV envelope glycoprotein gp110, wherein said cell line is selected from the group consisting of HIV-gp110-3, HIV-gp110-4, HIV-gp110-5, and HIV-gp110-6.

2. A monoclonal antibody produced by a cell line of claim 1.

3. A monoclonal antibody capable of specifically reacting with an antigenic determinant of HIV, wherein the monoclonal antibody specifically blocks the binding of an antibody produced by a cell line of claim 1.

4. A cell line that produces a monoclonal antibody which specifically reacts with an epitope of HIV envelope glycoprotein gp110, wherein said cell line is HIV-gp110-1 or HIV-gp110-2.

5. A monoclonal antibody produced by a cell line of claim 4.

6. A monoclonal antibody which specifically reacts with an antigenic determinant of HIV, wherein the monoclonal antibody specifically blocks the binding of a monoclonal antibody of claim 5.

7. A cell line that produces a monoclonal antibody which specifically reacts with an epitope of HIV core protein p25, wherein said cell line is HIV-p25-6 or HIV-p25-7.

8. A monoclonal antibody produced by a cell line of claim 7.

9. A monoclonal antibody which specifically reacts with a core antigenic determinant of HIV, wherein the monoclonal antibody specifically blocks the binding of a monoclonal antibody of claim 8.

10. A monoclonal antibody capable of reacting with an antigenic determinant of envelope glycoprotein gp110 of HIV wherein the antigenic determinant is within the region from about amino acid 301 to 336, comprising the sequence:

Cys—Thr—Arg—Pro—Asn—Asn—Asn—Thr—Arg—Lys—Ser—Ile—Arg
Arg—Gly—Pro—Gly—Arg—Ala—Phe—Val—Thr—Ile—Gly—Lys—Ile
Met—Arg—Gln—Ala—His—Cys, or homologs of said sequence.

11. A monoclonal antibody capable of reacting with an antigenic determinant of envelope glycoprotein gp110 of HIV wherein the antigenic determinant is within the region from about amino acid 308 to 328, comprising the sequence:

Thr—Arg—Lys—Ser—Ile—Arg—Ile—Gln—Arg—Gly—Pro—Gly—Arg—Ala—Phe—
Val—Thr—Ile—Gly—Lys—Ile, or homologs of said sequence.

12. A monoclonal antibody composition specifically reactive with an epitope of HIV within gp110 from about amino acid 301 to 336, comprising the sequence:

Cys—Thr—Arg—Pro—Asn—Asn—Asn—Thr—Arg—Lys—Ser—Ile—Arg—Ile—Gln—
Arg—Gly—Pro—Gly—Arg—Ala—Phe—Val—Thr—Ile—Gly—Lys—Ile—Gly—Asn—
Met—Arg—Gln—Ala—His—Cys, or homologs of said sequence wherein said monoclonal antibody is capable of neutralizing in vitro the infectivity of HIV.

13. A monoclonal antibody composition specifically reactive with an epitope of HIV within gp110 from about amino acid 308 to 328, comprising the amino acid sequence:

Thr—Arg—Lys—Ser—Ile—Arg—Ile—Gln—Arg—Gly—Pro—Gly—Arg—Ala—Phe—
Val—Thr—Ile—Gly—Lys—Ile, or homologs of said sequence, wherein said monoclonal antibody is capable of neutralizing in vitro the infectivity of HIV.

14. A monoclonal antibody composition comprising a first monoclonal antibody specifically reactive with an epitope of HIV wherein said epitope is encoded within the region comprising bp 7246 to bp 7317, encoding an amino acid sequence:

Val—Lys—Ile—Glu—Pro—Leu—Gly—Val—Ala—
Pro—Thr—Lys—Ala—Lys—Arg—
Arg—Val—Val—Gln—Arg—Glu—Lys—Arg—Ala, or homologs thereof, and a second monoclonal antibody specifically reactive with an epitope within HIV p25, wherein said composition neutralizes in vitro the infectivity of HIV.

15. The composition of claim 14, wherein the second monoclonal antibody reactive with an epitope within HIV p25 is reactive with an epitope within the region from about amino acids 278 to 319, and comprising the sequence:

Ser—Pro—Thr—Ser—Ile—Leu—Asp—Ile—Arg—Gln—Gly—Pro—Lys—Glu—Pro—
Phe—Arg—Asp—Tyr—Val—Asp—Arg—Phe—Tyr—Lys—Thr—Leu—Arg—Ala—Glu—

-continued

Gln—Ala—Ser—Gln—Glu—Val—Lys—Asn—Trp—Met—Thr—Glu, or within the region comprising amino acids 315 to 363, and comprising the sequence:

Asn—Trp—Met—Thr—Glu—Thr—Leu—Leu—Val—Gln—Asn—Ala—Asn—Pro—Asp—
Cys—Lys—Thr—Ile—Leu—Lys—Ala—Leu—Gly—Pro—Ala—Ala—Thr—Leu—Glu—
Glu—Met—Met—Thr—Ala—Cys—Gln—Gly—Val—Gly—Gly—Pro—Gly—His—Lys—
Ala—Arg—Val—Leu, or homologs of said sequences.

16. A monoclonal antibody composition comprising a first monoclonal antibody specifically reactive with an epitope of HIV p25 wherein said epitope is located within a region comprising amino acids 278 to 319, comprising the sequence:

Ser—Pro—Thr—Ser—Ile—Leu—Asp—Ile—Arg—Gln—Gly—Pro—Lys—Glu—Pro—
Phe—Arg—Asp—Tyr—Val—Asp—Arg—Phe—Tyr—Lys—Thr—Leu—Arg—Ala—Gly—
Gln—Ala—Ser—Gln—Gly—Val—Lys—Asn—Trp—Met—Thr—Glu, and a second a monoclonal antibody specifically reactive with an epitope of HIV p25 wherein said epitope is located within a region comprising amino acid 315 to 363, comprising the sequence:

Asn—Trp—Met—Thr—Glu—Thr—Leu—Leu—Val—Gln—Asn—Ala—Asn—Pro—Asp
Cys—Lys—Thr—Ile—Leu—Lys—Ala—Leu—Gly—Pro—Ala—Ala—Thr—Leu—Glu
Glu—Met—Met—Thr—Ala—Cys—Gln—Gly—Val—Gly—Gly—Pro—Gly—His—Lys
Ala—Arg—Val—Leu, or homologs of said sequence, wherein said composition is capable of neutralizing in vitro the infectivity of HIV.

17. A method for diagnosing the presence of HIV in a biological sample, comprising:
  incubating with said biological sample a monoclonal antibody capable of reacting with an antigenic determinant of HIV gp110 within the region comprising the amino acid sequence:

Val—Lys—Ile—Glu—Pro—Leu—Gly—Val—Ala—
          Pro—Thr—Lys—Ala—Lys—Arg—
Arg—Val—Val—Gln—Arg—Glu—Lys—Arg—Ala, or homologs thereof, wherein the monoclonal antibody is produced by cell line HIV-gp110-1 or HIV-gp110-2, or specifically blocks the binding of a monoclonal antibody from said cell lines; and detecting the presence of immune complexes formed between the monoclonal antibody and said HIV gp110 antigenic determinant in the biological sample, and therefrom determining the presence or absence of HIV in the sample.

* * * * *